(12) United States Patent
Johnson et al.

(10) Patent No.: US 11,090,181 B2
(45) Date of Patent: Aug. 17, 2021

(54) NASAL DILATORS

(71) Applicant: ASAP Breatheassist Pty Ltd, Armadale (AU)

(72) Inventors: Michael Ralph Burgess Johnson, Hawthorn (AU); Toby James Hartley, Ferntree Gully (AU); Ashley Mark Turner, Ashburton (AU)

(73) Assignee: ASAP Breatheassist Pty Ltd, Armadale (AU)

( * ) Notice: Subject to any disclaimer, the term of this patent is extended or adjusted under 35 U.S.C. 154(b) by 333 days.

(21) Appl. No.: 15/579,304

(22) PCT Filed: Jun. 5, 2015

(86) PCT No.: PCT/AU2015/050314
§ 371 (c)(1),
(2) Date: Dec. 4, 2017

(87) PCT Pub. No.: WO2016/191791
PCT Pub. Date: Dec. 8, 2016

(65) Prior Publication Data
US 2018/0168846 A1 Jun. 21, 2018

(51) Int. Cl.
*A61F 5/08* (2006.01)
*A61F 5/56* (2006.01)
*A62B 23/06* (2006.01)

(52) U.S. Cl.
CPC .................. *A61F 5/08* (2013.01); *A61F 5/56* (2013.01); *A62B 23/06* (2013.01)

(58) Field of Classification Search
CPC ... A61F 5/08; A61F 5/56; A61B 23/00; A61B 23/02; A61B 23/025; A61B 23/06;
(Continued)

(56) References Cited

U.S. PATENT DOCUMENTS

| 851,048 A | 4/1907 | Woodward |
| 1,034,566 A | 8/1912 | Barratt |

(Continued)

FOREIGN PATENT DOCUMENTS

| AU | 2013204827 A1 | 2/2014 |
| AU | 2013205674 A1 | 2/2014 |

(Continued)

OTHER PUBLICATIONS

International Search Report in International Application No. PCT/AU2015/050314, dated Aug. 12, 2015, 4 pages.

(Continued)

*Primary Examiner* — Diane D Yabut
*Assistant Examiner* — Christian D Knauss
(74) *Attorney, Agent, or Firm* — Servilla Whitney LLC

(57) ABSTRACT

Embodiments relate generally to a nasal dilator comprising a body for insertion into a nasal cavity of a nose. The body includes a loop structure having an inner surface, a reverse outer surface, a first side and a second side opposite to the first side. The inner surface defines an aperture and the reverse outer surface is configured for urging against a nasal passage wall of the nose. The body further includes an arm member having a first end coupled to the loop structure and a free end, the arm member extending outwardly from the loop structure and configured to extend along a nasal passage of the nasal cavity and engage with an internal surface of a nostril of the nose.

11 Claims, 14 Drawing Sheets

(58) Field of Classification Search
CPC .. A61M 16/20; A61M 16/204; A61M 16/205; A61M 16/206; A61M 16/208; A61M 2210/0618
See application file for complete search history.

(56) References Cited

U.S. PATENT DOCUMENTS

| | | | |
|---|---|---|---|
| 1,077,574 A | 11/1913 | Woodward | |
| 1,255,578 A | 2/1918 | Boxley | |
| 1,481,581 A | 1/1924 | Woodward | |
| 2,243,360 A | 5/1941 | Slatis et al. | |
| 3,710,799 A | 1/1973 | Caballero | |
| 3,722,509 A * | 3/1973 | Nebel | A62B 23/06 128/204.12 |
| 3,905,335 A * | 9/1975 | Kapp | A62B 23/06 128/206.11 |
| 4,414,977 A | 11/1983 | Rezakhany | |
| 4,576,168 A | 3/1986 | Jalowayski | |
| 4,592,357 A * | 6/1986 | Ersek | A61F 5/08 606/199 |
| 4,759,365 A | 7/1988 | Askinazy | |
| 5,059,193 A | 10/1991 | Kuslich | |
| 5,099,857 A | 3/1992 | Baldo et al. | |
| 5,423,858 A | 6/1995 | Bolanos et al. | |
| RE35,408 E | 12/1996 | Petruson | |
| 5,683,465 A | 11/1997 | Shinn et al. | |
| 5,693,100 A | 12/1997 | Pisharodi | |
| 5,787,884 A | 8/1998 | Tovey | |
| 5,895,409 A | 4/1999 | Mehdizadeh | |
| 5,931,852 A | 8/1999 | Brennan | |
| 5,955,376 A | 9/1999 | Tovey | |
| 6,109,262 A | 8/2000 | Tovey | |
| 6,129,763 A | 10/2000 | Chauvin et al. | |
| 6,270,512 B1 | 8/2001 | Rittmann | |
| 6,436,142 B1 | 8/2002 | Paes et al. | |
| 6,561,188 B1 | 5/2003 | Ellis | |
| 6,562,057 B2 | 5/2003 | Santin | |
| 6,626,179 B1 * | 9/2003 | Pedley | A61F 2/18 128/207.18 |
| 6,821,298 B1 | 11/2004 | Jackson | |
| 6,978,781 B1 | 12/2005 | Jordan | |
| 7,055,523 B1 | 6/2006 | Brown | |
| 7,105,008 B2 | 9/2006 | Maryanka | |
| 7,108,198 B2 | 9/2006 | Altadonna, Jr. | |
| 7,318,438 B2 | 1/2008 | Brown | |
| 7,390,331 B2 | 6/2008 | Santin et al. | |
| D575,397 S | 8/2008 | Noce | |
| 7,461,651 B2 | 12/2008 | Brown | |
| 7,727,252 B2 | 6/2010 | Maryanka | |
| 7,740,643 B2 | 6/2010 | Maryanka | |
| 7,918,224 B2 | 4/2011 | Dolezal et al. | |
| 8,048,102 B2 | 11/2011 | Brown | |
| D652,143 S | 1/2012 | Brown | |
| 8,262,688 B2 | 9/2012 | Santin et al. | |
| 8,403,954 B2 | 3/2013 | Santin et al. | |
| 8,491,622 B2 | 7/2013 | Brown | |
| 8,834,512 B1 | 9/2014 | Brown et al. | |
| D726,312 S | 4/2015 | Johnson | |
| D819,205 S | 5/2018 | Snyder | |
| 2003/0081639 A1 | 5/2003 | Duan et al. | |
| 2003/0086625 A1 | 5/2003 | Brennan | |
| 2003/0106555 A1 | 6/2003 | Tovey | |
| 2003/0144684 A1 | 7/2003 | Ogle | |
| 2004/0079814 A1 | 4/2004 | Altadonne, Jr. | |
| 2004/0111109 A1 | 6/2004 | Ruiz | |
| 2005/0021073 A1 | 1/2005 | Santin et al. | |
| 2005/0278028 A1 | 12/2005 | Mujwid | |
| 2006/0085027 A1 | 4/2006 | Santin et al. | |
| 2006/0185676 A1 | 8/2006 | Brown | |
| 2006/0185677 A1 | 8/2006 | Brown | |
| 2006/0207598 A1 | 9/2006 | Brown | |
| 2006/0259064 A1 | 11/2006 | Maryanka | |
| 2006/0266367 A1 | 11/2006 | Noce | |
| 2007/0107731 A1 | 5/2007 | Reed | |
| 2007/0283962 A1 | 12/2007 | Doshi et al. | |
| 2008/0167676 A1 | 7/2008 | Howard | |
| 2008/0178873 A1 | 7/2008 | Alpers | |
| 2009/0145441 A1 | 6/2009 | Doshi et al. | |
| 2009/0194100 A1 * | 8/2009 | Minagi | A61F 5/08 128/200.24 |
| 2009/0198268 A1 | 8/2009 | Case | |
| 2010/0042134 A1 | 2/2010 | Wien | |
| 2010/0063523 A1 | 3/2010 | Menard et al. | |
| 2010/0063532 A1 | 3/2010 | Moore | |
| 2010/0087749 A1 | 4/2010 | Tovey | |
| 2011/0118775 A1 | 5/2011 | Brown | |
| 2012/0111340 A1 * | 5/2012 | Robitaille | A61M 39/228 128/848 |
| 2012/0279504 A1 | 11/2012 | Moore | |
| 2012/0330345 A1 | 12/2012 | Tasca | |
| 2013/0081637 A1 | 4/2013 | Foley | |
| 2013/0211275 A1 | 8/2013 | Curti | |
| 2013/0296809 A1 | 11/2013 | Santin et al. | |
| 2014/0128904 A1 | 5/2014 | Mezzoli et al. | |
| 2014/0246023 A1 | 9/2014 | Maryanka | |
| 2015/0000675 A1 | 1/2015 | Kallikounis et al. | |
| 2015/0196420 A1 | 7/2015 | Ede et al. | |

FOREIGN PATENT DOCUMENTS

| | | | |
|---|---|---|---|
| CA | 2566268 A1 | 11/2004 | |
| CN | 101534755 A | 9/2009 | |
| CN | 102970943 A | 3/2013 | |
| CN | 103520815 A | 1/2014 | |
| CN | 203915751 U | 11/2014 | |
| CN | 104619377 A | 5/2015 | |
| EP | 1917993 A1 | 5/2008 | |
| EP | 2387978 A2 | 11/2011 | |
| EP | 2114326 B1 | 3/2014 | |
| EP | 1968684 B1 | 2/2016 | |
| JP | H11192251 A | 7/1999 | |
| KR | 100893945 B1 | 4/2009 | |
| KR | 20100096048 A | 9/2010 | |
| KR | 20120020335 A | 3/2012 | |
| WO | 88/09149 A1 | 12/1988 | |
| WO | 96/06657 A1 | 3/1996 | |
| WO | 96/07099 A1 | 3/1996 | |
| WO | 99/36773 A1 | 7/1999 | |
| WO | 00/78223 A1 | 12/2000 | |
| WO | 01/62342 A1 | 8/2001 | |
| WO | 02/31465 A1 | 4/2002 | |
| WO | 02/059569 A1 | 8/2002 | |
| WO | 2004026391 A1 | 4/2004 | |
| WO | 2007119041 A1 | 10/2007 | |
| WO | 2008/091782 A2 | 7/2008 | |
| WO | 2008109873 A2 | 9/2008 | |
| WO | 2009/124567 A1 | 10/2009 | |
| WO | 2011/104660 A2 | 9/2011 | |
| WO | 2012/137182 A2 | 10/2012 | |
| WO | 2014015359 A1 | 1/2014 | |
| WO | WO-2014183966 A1 * | 11/2014 | A61F 5/08 |

OTHER PUBLICATIONS

Written Opinion of the International Searching Authority in International Application No. PCT/AU2015/050314, dated Aug. 12, 2015, 4 pages.
International Preliminary Report on Patentability in Int. Appln. No. PCT/AU2016/050621, completed Nov. 21, 2017, 22 pages.
International Preliminary Report on Patentability in PCT/AU2014/000649, dated Oct. 12, 2016, 5 pages.
International Preliminary Report on Patentability in PCT/AU2015/050032, dated Dec. 20, 2016, 4 pages.
International Search Report in Int. Appln. No. PCT/AU2016/050621, dated Oct. 25, 2016, 7 pages.
International Search Report in PCT/AU2014/000649, dated Sep. 18, 2014, 7 pages.
International Search Report in PCT/AU2015/050032, dated Apr. 17, 2015, 5 pages.
Non-Final Office Action in U.S. Appl. No. 15/319,940, dated Apr. 6, 2018, 41 pages.

(56) References Cited

OTHER PUBLICATIONS

Non-Final Office Action in U.S. Appl. No. 15/319,941, dated Apr. 11, 2018, 50 pages.
Written Opinion of the International Searching Authority in Int. Appln. No. PCT/AU2016/050621, dated Oct. 25, 2016, 7 pages.
Written Opinion of the International Searching Authority in PCT/AU2014/000649, dated Sep. 18, 2014, 7 pages.
Written Opinion of the International Searching Authority in PCT/AU2015/050032, dated Apr. 17, 2015, 3 pages.
Airware Labs, retrieved from the internet Jul. 9, 2018, <URL: https://web.archive.org/web/20120522113321/http://www.airwarelab.com/>, published Mar. 22, 2012, 5 pages.
Breathe EZ Anti-Snoring Medical Nasal Device—Snoring Cure, retrieved from the internet on Jul. 9, 2018, <URL: https://web.archive.org/web/20120618221246/http://www.snoringcure.ca/breathe_ez_nasal_anti_snoring_medical_device.htm>, published May 14, 2007, 1 page.
Breathe-Aide, retrieved from the internet Jul. 9, 2018, <URL: https://web.archive.org/web/20141108204923/http://breatheaide.fm.alibaba.com/>, published Nov. 8, 2014, 1 page.
Breathe-Ezy Nasal Filters, retrieved from the internet Jul. 9, 2018, <URL: https://web.archive.org/web/20120615192635/http://www.breathe-ezy.com.au/>, published Apr. 29, 2005, 6 pages.
Breathing Relief Nasal Dilator, retrieved from the internet Jul. 9, 2018, <URL: https://web.archive.org/web/20120413210250/http://www.breathingrelief.com/>, published Jun. 16, 2006, 2 pages.
ClipAir® Anti-Snoring Nasal Dilator Device/Contre le Ronflement, retrieved from the internet on Jul. 9, 2018, <URL: https://web.archive.org/web/20120618061055/http://www.snoringcure.ca/clipair_nasal_anti_snoring_medical_dilator_device.htm>, published Aug. 1, 2010, 2 pages.
Flents Breathe Quiet! Nasal Dilator—Stop Snoring!, retrieved from the Internet on Jul. 9, 2018, <URL: https://web.archive.org/web/20120425220535/http://www.amazon.com/Flents-Breathe-Quiet-Nasal-Dilator/dp/B0019IHLR2>, published Aug. 29, 2010, 4 pages.
Flents Breathe Well Nasal Dilator—The Alternative to Nasal Strips, retrieved from the internet Jul. 9, 2018, <URL: https://web.archive.org/web/20120411195907/http://www.amazon.com/Flents-Breathe-Well-Nasal-Dialator/dp/B001J4K5E2>, published Feb. 2, 2009, 4 pages.
Inhalclip, retrieved from the internet Jul. 9, 2018, <URL: https://web.archive.org/web/20120413113017/http://www.oscimedsa.com/Stress_insomnie_stop>, published Oct. 21, 2010, 3 pages.
International Preliminary Examination Report in PCT/AU2003/000504 dated Feb. 2, 2005, 36 pages.
Max-Air Nose Cones, retrieved from the Internet Jul. 9, 2018, <URL: https://web.archive.org/web/20120725110753/http://www.maxairnosecones.com/max-air-nose-cones>, published Feb. 13, 2011, 8 pages.
Megavent Nasal Dilator, retrieved from the Internet Jul. 9, 2018, <URL: http://www.wellnessproducts.ch/?lan=en&page=2&id=66999>, published Jun. 26, 2012, 3 pages.
Nasal Pass Dilator, retrieved from the Internet Jul. 9, 2018, <URL: https://web.archive.org/web/20120630121946/http://nasalpass.com/contact_us.htm>, published Apr. 21, 2006, 1 pages.
Nasilator, The Science of Better Breathing, retrieved from the Internet Jul. 17, 2018, <URL: https://web.archive.org/web/20121219024329/http://www.nasilator.com/home.aspx>, published Sep. 6, 2012, 1 page.
Non-Final Office Action in U.S. Appl. No. 10/631,415 dated Aug. 18, 2005, 15 pages.
Non-Final Office Action in U.S. Appl. No. 10/631,415 dated Dec. 29, 2005, 9 pages.
Non-Final Office Action in U.S. Appl. No. 11/363,884 dated May 14, 2009, 9 pages.
Non-Final Office Action in U.S. Appl. No. 11/363,924 dated Apr. 13, 2009, 9 pages.
Non-Final Office Action in U.S. Appl. No. 12/154,868 dated Oct. 23, 2014, 35 pages.
Noseglobes, retrieved from the internet Jul. 9, 2018, <URL:https://web.archive.org/web/20110128162352/http://noseglobes.com/>, published Jan. 28, 2011, 1 page.
Nozovent® Anti-Snoring Medical Nasal Dilator Device, retrieved from the Internet on Jul. 9, 2018, <URL: https://web.archive.org/web/20120619012956/http://www.snoringcure.ca/nozovent_nasal_anti_snoring_medical_dilator_device.htm>, published Jul. 13, 2007, 2 pages.
Original Breathe Fit Snoring Aid Nasal Dilator, by Breathe Fit Nasal Dilator, retrieved from the internet on Jul. 9, 2018: <URL: https://web.archive.org/web/20120619035547/http://www.amazon.com/Originai-Breathe-Fit-Nasal-Dilator/dp/B0012RMWC4>, published Aug. 21, 2009, 5 pages.
Sanispira Dpi, retrieved from the internet Jul. 9, 2018, <URL: https://web.archive.org/web/20120712044423/http://www.sanispira.it/eng/index.php>, published Mar. 4, 2011, 3 pages.
Sinus Cones, retrieved from the Internet Jul. 9, 2018, <URL: https://web.archive.org/web/20120206054639/http://www.sanostec.com/code/productinfo.htm>, published Sep. 8, 2004, 2 pages.
SleepRight, retrieved from the internet Jul. 11, 2018, <URL: http://www.sleepright.com/nasal-breathe-aid.php, published Jun. 17, 2013, 6 pages.
Snore Free, retrieved from the internet Jul. 9, 2018, <URL: https://web.archive.org/web/20120614222005/http://www.magnetictherapy.co.uk/scp/SPECIALITY_PRODUCTS/SNORE_FREE.html>, published Dec. 8, 2004, 2 pages.
Snore Pin, Sleep Apnea Snoring Treatment, retrieved from the Internet Jul. 17, 2018, <URL: https://web.archive.org/web/20130111010828/http://omnisleep.in/snore-pin.html>, published Jan. 11, 2013, 2 pages.
Snoreben, retrieved from the internet Jul. 9, 2018, <URL: http://www.benmedical.com.au/>, published Jan. 2011, 2 pages.
Snoregem, British Snoring & Sleep Apnoea Associate, retrieved from the internet Jul. 9, 2018, <URL: https://web.archive.org/web/20120627060249/http://www.britishsnoring.co.uk/shop/snoregem.php>, published Jul. 3, 2010, 2 pages.
Snore-no-More, retrieved from the internet Jul. 9, 2018, <URL: https://web.archive.org/web/20120626140524/http://www.britishsnoring.co.uk/shop/nasal_dilators/snore_no_more.php?>, published Dec. 12, 2005, 1 pages.
Surgical Nostril Retainers, Porex Surgical Products Group, retrieved from the internet Jul. 17, 2018, <URL: https://web.archive.org/web/20051217233845/https://www.porexsurgical.com/English/surgical/sprodnoseother.asp>, published Dec. 19, 2005, 2 pages.
Ultimate Nasal Dilator, retrieved from the internet Jul. 9, 2018, <URL: https://web.archive.org/web/20120718070024/http://www.nasalaid.com/>, published Oct. 28, 2007, 1 page.
WoodyKnows—Super Nasal Filter for Allergy Relief, retrieved from the internet Jul. 17, 2018, <URL: https://web.archive.org/web/20120818163139/http://www.woodyknows.com:80/>, published Aug. 18, 2012, 3 pages.
Final Office Action in U.S. Appl. No. 15/319,940 dated Jan. 7, 2020, 25 pages.
Final Office Action in U.S. Appl. No. 15/319,941 dated Mar. 3, 2020, 41 pages.
English translation of search report in CN2015800807102 dated Oct. 22, 2020, 2 pages.
Final Office Action in U.S. Appl. No. 15/319,940, dated May 18, 2021, 12 pages.
Final Office Action in U.S. Appl. No. 15/319,941, dated May 18, 2021, 13 pages.
Non-Final Office Action in U.S. Appl. No. 15/748,698, dated Mar. 22, 2021, 26 pages.

\* cited by examiner

NASAL DILATORS

CROSS REFERENCE TO RELATED APPLICATIONS

This is a National Phase entry of International Application No. PCT/AU2015/050314, filed Jun. 5, 2015, the disclosure of which is incorporated herein by reference in its entirety.

TECHNICAL FIELD

Described embodiments generally relate to nasal dilators for facilitating respiration. Some embodiments relate to a nasal dilator having a dual dilation mechanism configured to perform dual or concurrent dilation of the nostril of the user. Some embodiments relate to a nasal dilator having a valve mechanism to allow control of inhalation and exhalation through the nose. Some embodiments relate to a nasal dilator having a filtration mechanism to filter airflow during respiration.

BACKGROUND

Nasal dilator devices are typically worn by users to dilate their nasal cavities when sleeping and/or partaking in sporting activities to thereby facilitate respiration.

It is desired to address or ameliorate one or more shortcomings of known nasal dilator devices, or to at least provide a useful alternative thereto.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Some embodiments relate to a nasal dilator comprising a body for insertion into a nasal cavity of a nose, the body including: a loop structure having an inner surface, a reverse outer surface, a first side and a second side opposite to the first side, wherein the inner surface defines an aperture and the reverse outer surface is configured for urging against a nasal passage wall of the nose; and an arm member having a first end coupled to the loop structure and a free end, the arm member extending outwardly from the loop structure and configured to extend along a nasal passage of the nasal cavity and engage with an internal surface of a nostril of the nose.

In some embodiments, the nasal dilator may further comprise a leg member extending outwardly from the loop structure and configured to protrude from the nasal cavity of the user. For example, the arm member may extend from the first side of the loop structure and the leg member may extend from the second side of the loop structure.

In some embodiments, the loop structure may comprise an adjustment mechanism to allow for selective expansion and contraction of the loop structure. The adjustment mechanism may comprise a pin and a socket arranged to receive and engage the pin. For example, the pin and socket may extend from the inner surface of the loop structure toward each other and are configured to engage with one another to allow the adjustment mechanism to span the aperture defined by the loop structure. Alternatively, or in addition, a first length of the loop structure may comprise the pin and a second length of the loop structure may comprise the socket. In some embodiments, the adjustment mechanism may comprise a belt and a sleeve arranged to receive and engage the belt, the belt extending from a first end of the loop structure into the sleeve provided at a second end of the loop structure.

The body may comprise a platform spanning the aperture defined by the inner surface of the loop structure. The platform may be releasably coupled to the inner surface of the loop structure. In some embodiments, the platform may comprise a filter.

In some embodiments, the nasal dilator comprises a valve mechanism for controlling fluid flow through the aperture which may include a seal supported by the platform and configured to span the aperture defined by the inner surface of the loop structure. For example, the seal may include a flap configured to transition between an open state, whereby fluid may be conveyed through the platform, and a closed state, whereby fluid may be hindered from being conveyed through the platform by the flap and wherein an orifice may be disposed in the seal. Alternatively, the seal may include a ball valve configured to transition between an open state, whereby fluid may be conveyed through the platform, and a closed state, whereby fluid may be hindered from being conveyed through the platform by the ball valve and wherein an orifice may be disposed in the seal. In some embodiments, the valve mechanism may comprise a collar extending from the second side of the loop structure and forming a seal with the loop structure.

In some embodiments, the arm member may be moveably coupled to the loop structure to allow selective positioning of the arm member. For example, the arm member may be rotatably coupled or hingedly coupled to the loop structure to allow selective positioning of the arm member. In some embodiments, the arm member may comprise a ball and socket joint to couple the arm member to the loop structure. The arm member may comprise a nostril engaging element at the free end to engage with the internal surface of the nostril. The nostril engaging element may comprise a series of protrusions disposed on the nostril engaging element.

In some embodiments, the loop structure may comprise a chamber arranged to receive at least one of a compound and a medicament. In some embodiments, the loop structure may comprise an outer layer disposed along at least a portion of the outer surface of the loop structure. The outer layer may be or comprise a deformable material. The deformable material may comprise at least one of memory foam, an overmould, and an inflatable tube. In some embodiments, the outer layer may comprise at least one protruding flange portion extending along at least a section of the outer surface of the loop structure. The outer layer may be infused with at least one of a compound, a medicament, a fragrance, and an aromatic agent.

In some embodiments, a film including a compound may be disposed on the loop structure and may be provided with a removable seal to mitigate release of the compound from the film. In some embodiments, a coating is disposed on the loop structure and is arranged to release a scent in response to abrasion of the coating.

Some embodiments relate to a nasal dilator comprising a body for insertion into a nasal cavity of a nose, the body including a loop structure having an inner surface and a reverse outer surface, wherein the inner surface defines an aperture; and an arm member, the arm member extending outwardly from the loop structure; wherein the outer surface of the loop structure is arranged, in use, to urge against a nasal cavity wall in proximity to a nasal vestibule of the nose to allow dilation of the nostril and the arm member is arranged, in use, to extend along the nasal passage and to engage with an internal surface of the nostril.

In some embodiments, the arm member may extend beyond a perimeter of the loop structure and may be configured, in use, to exert an outward force on the internal surface of the nostril to thereby stent and/or dilate the nostril. In some embodiments, in use, the arm member may engage the internal surface of the nostril at a junction of the greater alar cartilage and lateral nasal cartilage to thereby provide improved support for dilation of the nasal passage. In some embodiments, in use, the outer surface of the loop structure urges against the nasal cavity wall to allow the loop structure to concentrically engage with the nasal cavity wall.

Some embodiments relate to a nasal dilator device comprising a first and second nasal dilator as described above, wherein the first and second nasal dilators are coupled together.

BRIEF DESCRIPTION OF DRAWINGS

Embodiments are described in further detail below, by way of example, with reference to the accompanying drawings, in which.

DESCRIPTION OF EMBODIMENTS

Described embodiments generally relate to nasal dilators for facilitating respiration. Some embodiments relate to a nasal dilator having a dual dilation mechanism configured to perform dual or concurrent dilation of the nostril of the user. Some embodiments relate to a nasal dilator having a valve mechanism to allow control of inhalation and exhalation through the nose. Some embodiments relate to a nasal dilator having a filtration mechanism to filter airflow during respiration.

Figure 1:
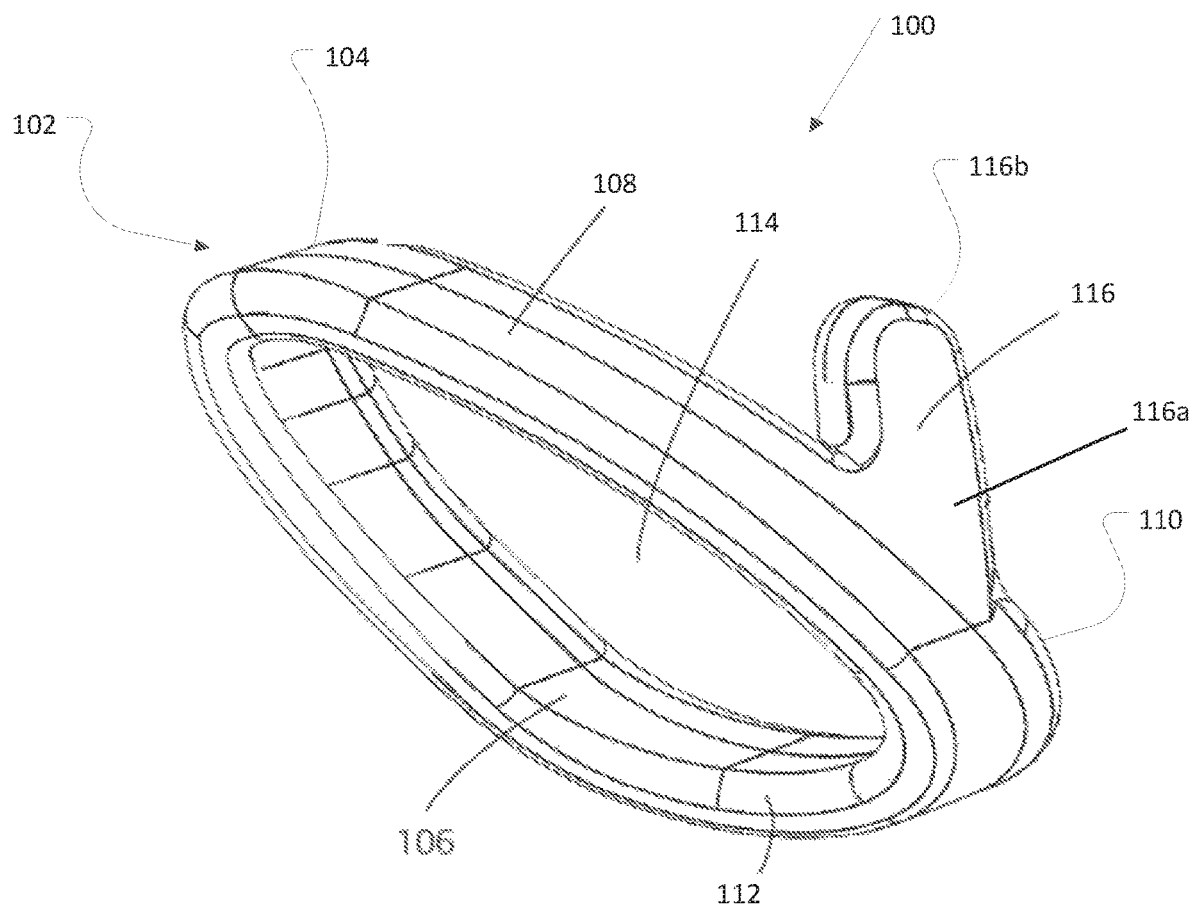
FIG. 1 is a is side perspective view of a nasal dilator, according to some embodiments.
Figure 2A:
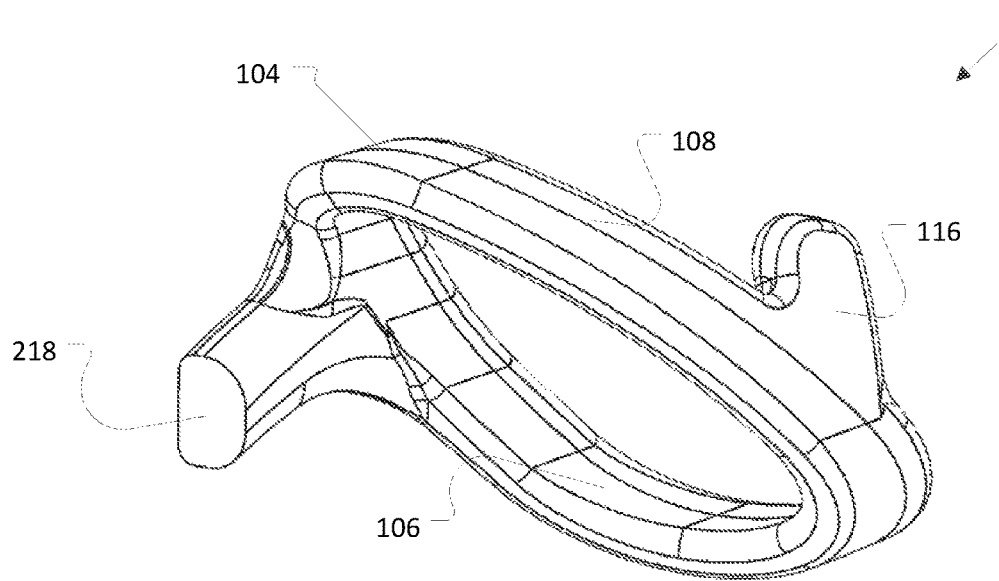
FIG. 2A is a front perspective view of a nasal dilator, according to some embodiments.
Figure 2B:
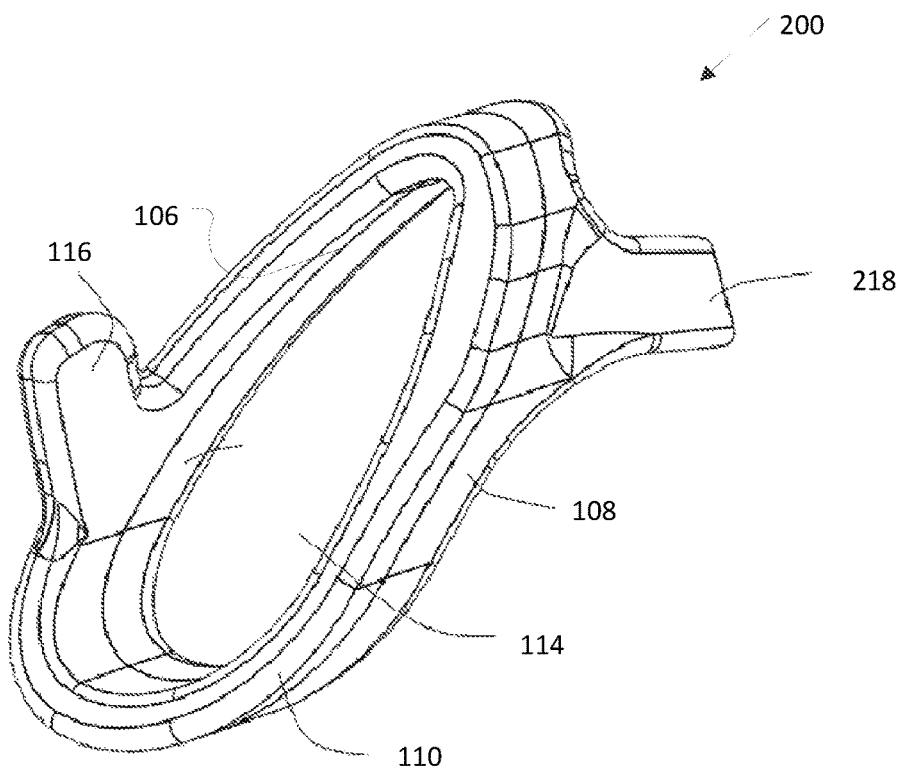
FIG. 2B is a rear perspective view of the nasal dilator of FIG. 2A.
Figure 2C:
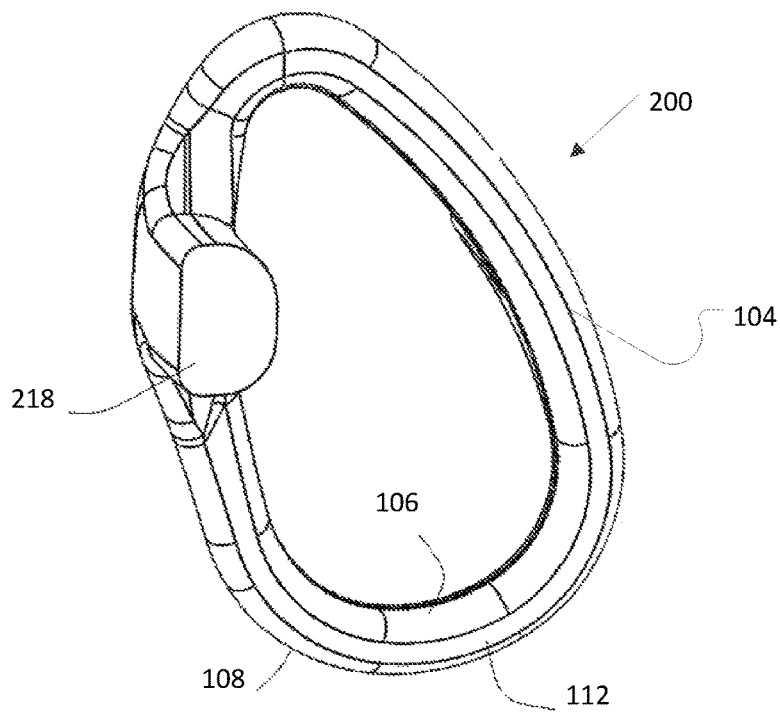
FIG. 2C is a front view of the nasal dilator of FIG. 2A.
Figure 2D:
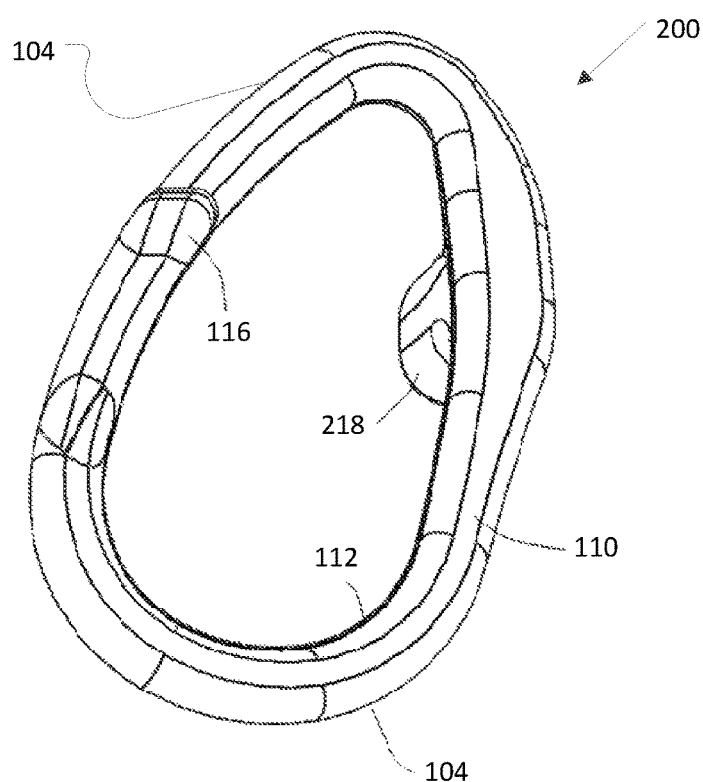
FIG. 2D is a rear view of the nasal dilator of FIG. 2A.
Figure 3A:
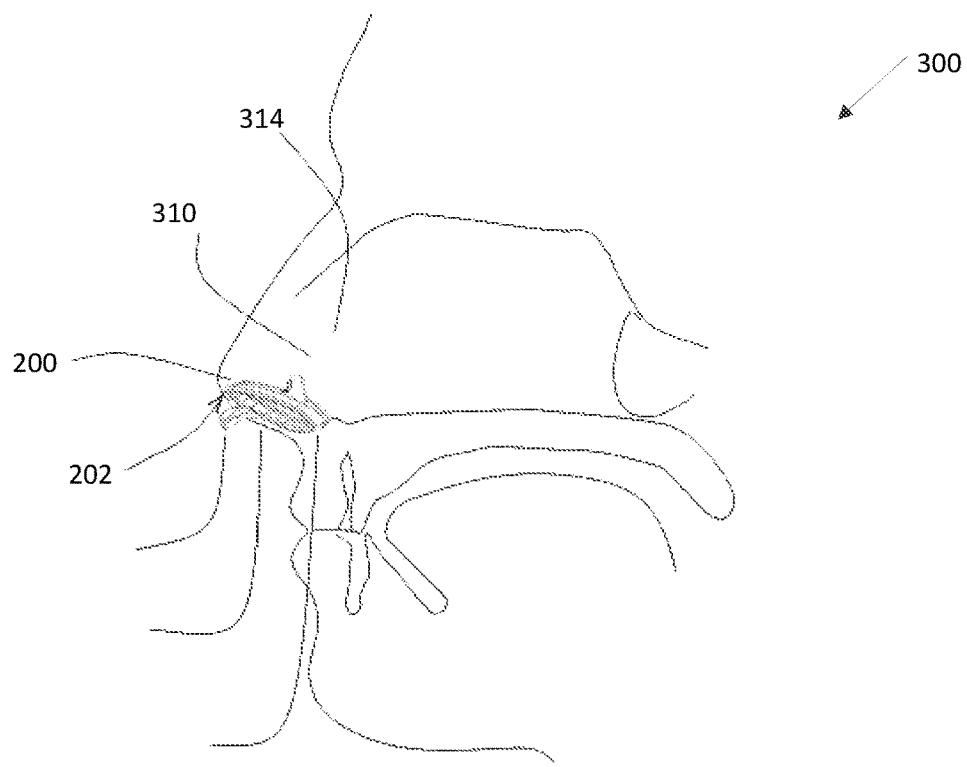
FIG. 3A is a side view of a user wearing or donning the nasal dilator of FIGS. 2A to 2D.
Figure 3B:
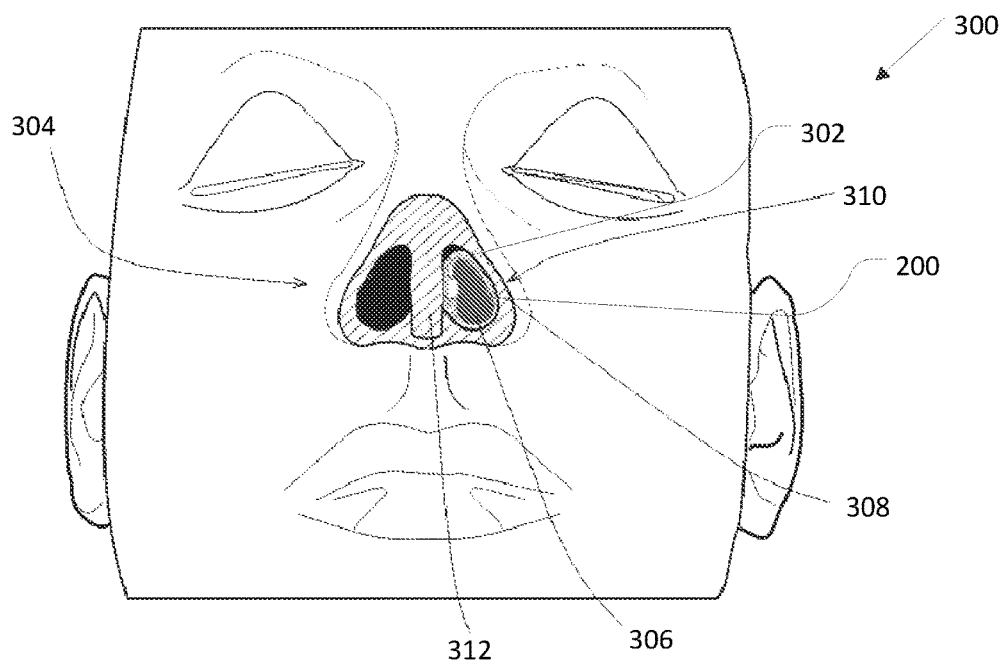
FIG. 3B is a front view of the user of FIG. 3A wearing or donning the nasal dilator device 200 of FIGS. 2A to 2D.
Figure 3C:
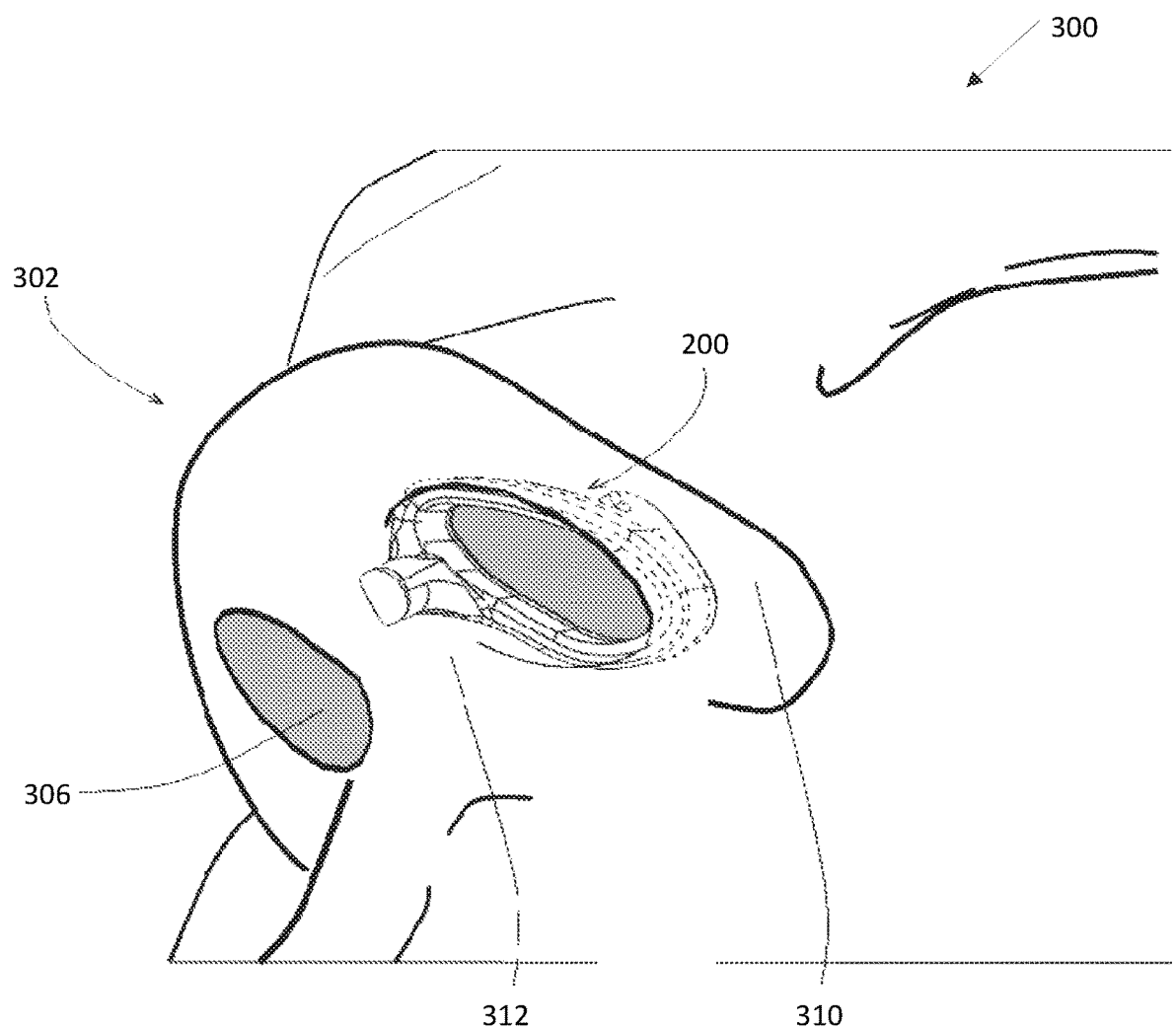
FIG. 3C is a bottom perspective view of the user of FIG. 3A, wearing or donning the nasal dilator device 200 of FIGS. 2A to 2D.

Referring to FIG. 1, there is illustrated a nasal dilator, generally indicated at 100. The nasal dilator 100 comprises a body 102 for insertion into a nasal cavity of a nose of a user, as shown in FIGS. 3A to 3C. The body 102 comprises a loop structure 104 having an inner surface 106 and a reverse outer surface 108. For example, the inner surface 106 may be a first major surface of the loop structure 104 and the outer surface 108 may be a second major surface of the loop structure 104, opposite to or reverse from the first major surface. The loop structure 104 may further comprise a first side 110, or first minor surface, and a second side 112, or second minor surface, opposite to or reverse from the first side 110.

The inner surface 106 of the loop structure 104 defines an aperture 114. For example, the aperture may be substantially round, teardrop or oval in shape. The outer surface 108 of the loop structure 104 is configured for urging against a nasal passage wall of a nose. For example, in use and as shown in FIGS. 3A to 3C, the outer surface 108 of the loop structure 104 may urge against the nasal passage wall 302 of the nose 304 to thereby dilate the nostrils of the nose 304. In some embodiments, the outer surface 108 of the loop structure 104 may be sized and configured to substantially form a seal with the nasal passage wall 302.

As illustrated in FIG. 1, the nasal dilator 100 comprises an arm member 116 extending outwardly from the loop structure 104 and arranged to engage with a nostril of the nose of a user. In some embodiments, the arm member 116 may extend from the first side 110 of the loop structure 104. The arm member 116 may be configured to extend along a nasal passage of the nasal cavity and engage with the internal surface of the nostril. The arm member 116 may have a first end 116a coupled to, for example, attached to or integrally formed with, the first side 110 of the loop structure 104 and a free end 116b opposite to the first end 116a. In some embodiments, the loop structure 104 may extend in a first plane and the arm member 116 may extend in a second plane substantially orthogonal to the first plane.

In some embodiments, the arm member 116 may be configured to exert an outward force on the internal surface of the nostril of the user to thereby stent and/or dilate the nostril. For example, the arm member 116 may protrude outwardly beyond a perimeter of the loop structure 104 and/or may be resiliently biased to an outward deflecting configuration. In some embodiments, the arm member 116 may be flexible and resiliently biased away from the loop structure 104 to allow the arm member 116 to be compressed for insertion into the nose of a user and to reform once placed inside the nose to thereby dilate the nostrils, as illustrated in FIGS. 3A to 3C. In use, the arm member 116 is configured to engage the internal surface of the nostril at a junction of the greater alar cartilage and lateral nasal cartilage (not shown), when the nasal dilator 100 appropriately placed in the nostril, to thereby stent or dilate the nasal passage.

The loop structure 104 and the arm member 116 of the nasal dilator 100 may cooperate as a dual dilation mechanism configured to perform dual or concurrent dilation of the nostril of the user.

Referring to FIGS. 2A to 2D, there is illustrated a nasal dilator, generally indicated at 200, according to some embodiments. The nasal dilator 200 may comprise similar components and elements to those of nasal dilator 100 depicted in FIG. 1 and accordingly those similar components and elements are denoted by like numerals. Specifically, the nasal dilator 200 comprises a body 202 for insertion into a nasal cavity of a nose of a user, as shown in FIGS. 3A to 3C. The body 202 comprises a loop structure that is the same as or similar to the loop structure 104 and has an inner surface 106 and a reverse outer surface 108.

As illustrated in FIGS. 2A to 2D, the nasal dilator 200 further comprises a leg member 218 extending outwardly from the loop structure 104. In some embodiments, the leg member 218 may extend from the second side 112 of the loop structure 104. The leg member 218 may be configured to protrude from the nose of the user in use and may be employed to hold the nasal dilator 200 and to position and adjust the nasal dilator 200 in the nasal cavity of the nose of a user.

FIGS. 3A to 3C show views of a user 300 wearing or donning the nasal dilator 200 of FIGS. 2A to 2D. As depicted, the nasal dilator 200 is sized and configured to be orientated such that the outer surface 108 of the loop structure 104 engages with and urges against a nasal passage wall 302 of the nose 304, for example, toward a front portion of the nasal passage 306 and the arm member 116 extends along the nasal passage 306 and engages with an internal surface 308 of the nostril 310, for example, at or in proximity to the alar valve region 314. As best shown in FIG. 3A, the body 202 of the nasal dilator 200 may be configured to rest on a nasal passage floor 312 and the leg member 218 may emerge from the nostril 310 adjacent to a septum 314 of the nose 304, to allow positioning and/or adjustment of the nasal dilator 200 by the user. In this way, the nasal dilator 200 may be securely retained within the nasal passage 306 with little or no pinching of or pressure being exerted on the septum 314. Furthermore, the loop structure 104 may be configured in size and shape to accommodate various shapes and sizes of noses.

Figure 4:
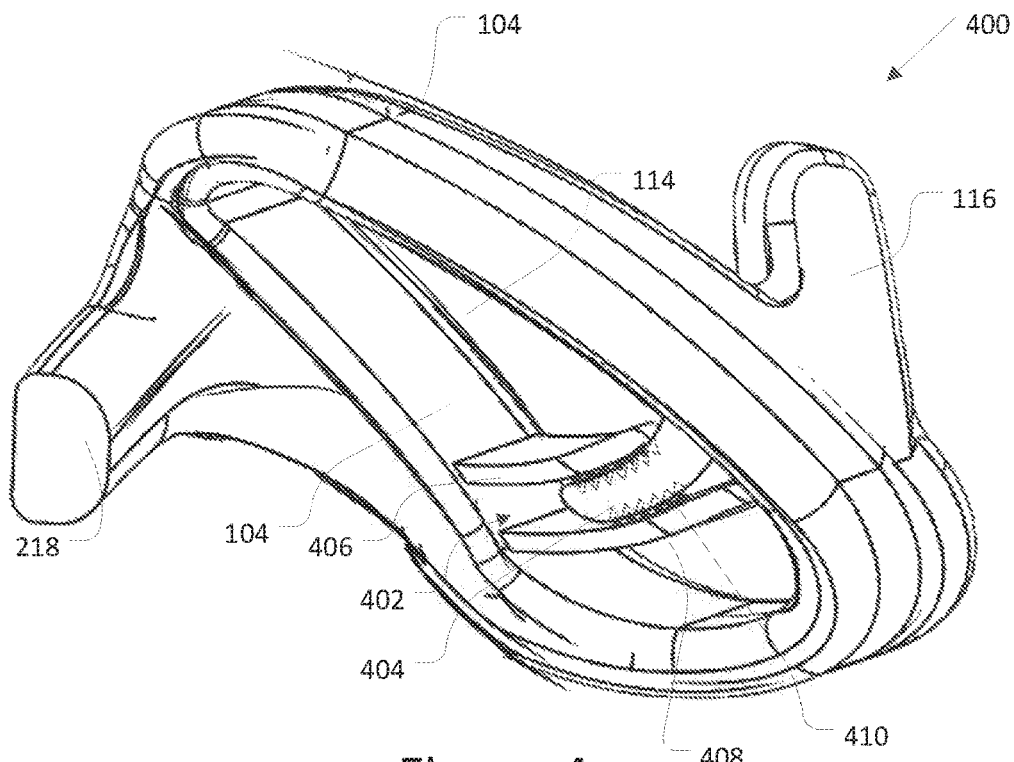
FIG. 4 is a front perspective view of a nasal dilator including an adjustment mechanism, according to some embodiments.
Figure 5:
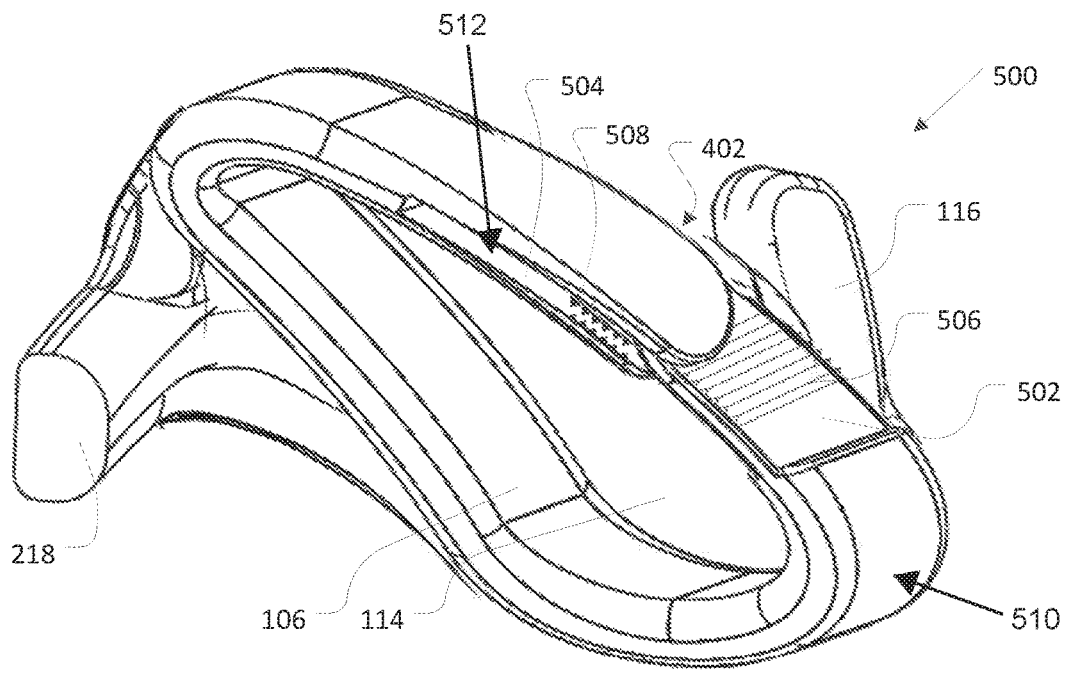
FIG. 5 is a front perspective view of a nasal dilator including an adjustment mechanism, according to some embodiments.
Figure 6:
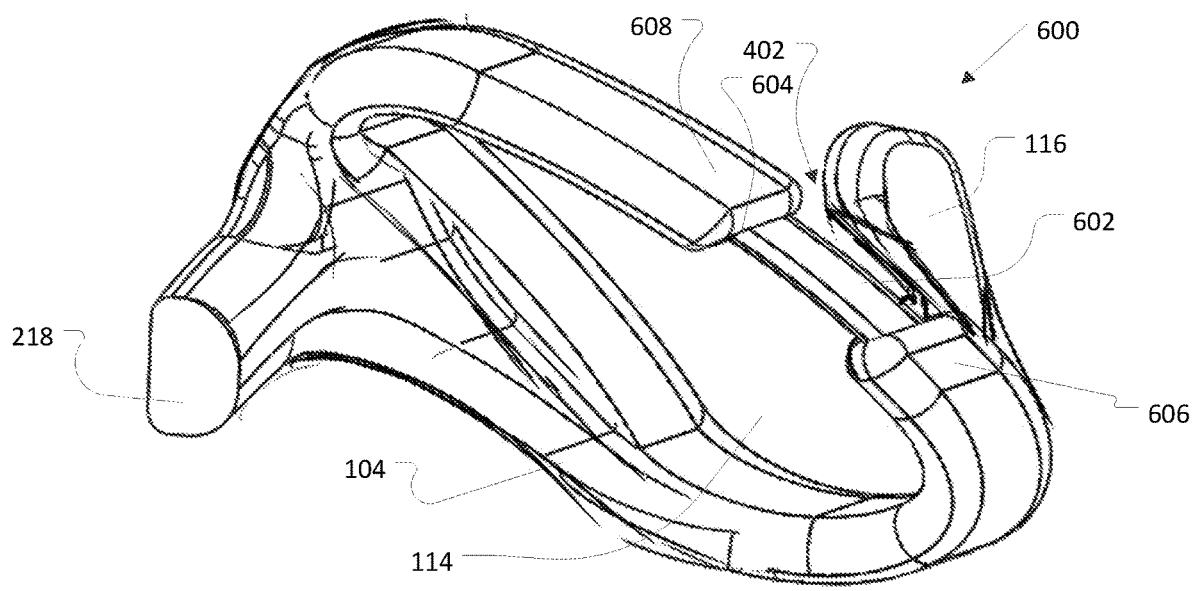
FIG. 6 is a front perspective view of a nasal dilator including an adjustment mechanism, according to some embodiments.

Referring now to FIGS. 4, 5 and 6, there are illustrated nasal dilators, generally indicated at 400, 500 and 600, respectively, according to some embodiments. The nasal dilators 400, 500 and 600 may comprise similar components and elements to those of nasal dilator 200 depicted in FIGS. 2A to 2D and accordingly those similar components and elements are denoted by like numerals.

As shown in FIGS. 4, 5 and 6, the nasal dilators 400, 500 and 600 each comprise an adjustment mechanism 402 to allow for adjustment of the loop structure 104, for example, to thereby adjust a size and/or shape of the aperture 114. For example, the adjustment mechanism 402 may enable selective adjustment of the loop structure 104, allowing the loop structure 104 to be selectively dilated or expanded and contracted. For example, the adjustment mechanism 402 may comprise a mating or interlocking mechanism whereby application of sufficient force to the adjustment mechanism 402 may be effective to overcome a restriction or friction force provided by the structure of the mechanism 402. In such embodiments, the material of the body of the dilator 400, 500 or 600 is selected to be sufficiently elastically deflectable to allow manual adjustment.

In some embodiments, for example as depicted in FIG. 4, the adjustment mechanism 402 comprises a pin 404 and a socket 406 that is arranged to receive and engage with the pin 404. For example, the pin 404 may comprise serrations or protrusions 408 and the socket 406 may comprise complementary grooves or ridges 410 for adjustable engagement with the serrations or protrusions 408. In some embodiments, the pin 404 and socket 406 extend from the inner surface 106 of the loop structure 104 toward each other. For example, the pin 404 and socket 406 may be configured to engage with one another to thereby allow the adjustment mechanism to span the aperture 114 defined by the loop structure 104.

The pin 404 may be fully or substantially fully inserted into the socket 406 to enable the loop structure 104 to adopt or assume a fully contracted or substantially fully contracted state. The pin 404 may be partially inserted into the socket 406 to enable the loop structure 104 to adopt or assume only a partially contracted state or more dilated state, to provide for greater dilation of the loop structure 104 and to accommodate variations in nasal passage sizes.

Referring to FIG. 5, there is illustrated a nasal dilator, generally indicated at 500, according to some embodiments. The nasal dilator 500 may comprise similar components and elements to those of nasal dilator 200 as depicted in FIGS. 2A to 2D and accordingly those similar components and elements are denoted by like numerals.

In some embodiments, as depicted in FIG. 5, the adjustment mechanism 402 comprises a pin 502 and a socket 504 arranged to receive and engage the pin 502. For example, the pin 502 may comprise serrations or protrusions 506 and the socket 504 may comprise grooves or ridges 508 for adjustable engagement with protrusions 506. In some embodiments, a first portion 510 or length of the loop structure 104 may comprise the pin 502 and a second portion 512 or length of the loop structure 104 may comprise the socket 504 configured to receive the pin 502. The protrusions 506 may be disposed on the outer surface 108 of the loop structure 104. The pin 502 and socket 504 may be configured to engage with one another to thereby loosen and/or tighten the loop structure 104, thereby enabling the loop structure 104 to be selectively dilated or expanded and contracted.

The pin 502 may be fully or substantially fully inserted into the socket 504 to enable the loop structure 104 to adopt or assume a fully contracted or substantially fully contracted state. The pin 502 may be partially inserted into the socket 504 to enable the loop structure 104 to adopt or assume only a partially contracted state or more dilated state, to provide for greater dilation of the loop structure 104 and to accommodate variations in nasal passage sizes.

In some embodiments, as depicted in FIG. 6, the adjustment mechanism 402 comprises a belt 602 and a sleeve 604 that is arranged to receive and engage the belt 602. In some embodiments, the loop structure 104 comprises the belt 602, which extends from a first end 606 of the loop structure 104 to the sleeve 604 at a second end 608 of the loop structure 104 to thereby define the aperture 114. For example, the sleeve 604 may extend into and be defined by the second end 608 of the loop structure 104. In some embodiments the belt 602 may comprise serrations or protrusions (not shown) and the sleeve 604 may comprise grooves or ridges (not shown) for adjustable engagement with protrusions.

The belt 602 may be fully or substantially fully inserted into the sleeve 604 to enable the loop structure 104 to adopt or assume a fully contracted or substantially fully contracted state and decreasing the size of the aperture 114. The belt 602 also may be partially inserted into the sleeve 604 to enable the loop structure 104 to adopt or assume only a partially contracted state or more dilated state, to provide for greater dilation of the loop structure 104 and to accommodate variations in nasal passage sizes.

The adjustment mechanism 402 allows the size of the aperture 114 of the loop structure 104 of the nasal dilator 400, 500 and 600 to be adjusted by the user, for example, to provide for a more suitably and comfortable fit prior to insertion. In some embodiments, the adjustment mechanism 402 may be configured to self-adjust during insertion and positioning by the user. For example, with reference to FIG. 5, upon insertion of nasal dilator 500, the loop structure 104 may constrict in size in response to exertion of a force on the adjustment mechanism 402 by the nasal passage 306.

Figure 7:
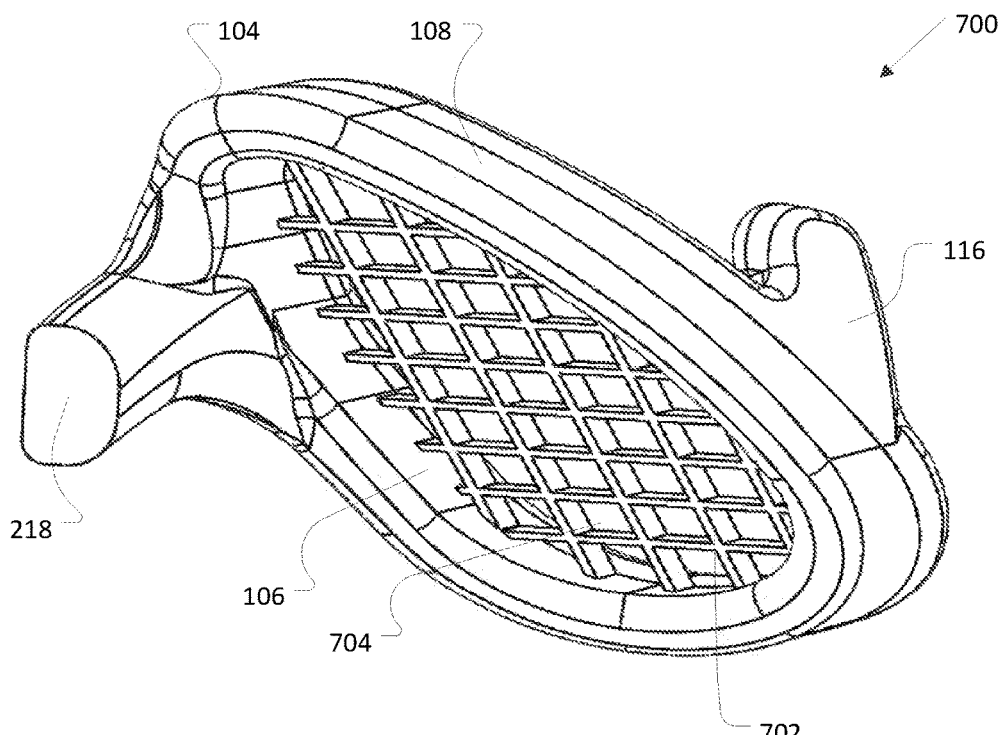
FIG. 7 is a front perspective view of a nasal dilator including a platform, according to some embodiments.

Referring to FIG. 7, there is illustrated a nasal dilator, generally indicated at 700, according to some embodiments. The nasal dilator 700 may comprise similar components and elements to those of nasal dilator 200 as depicted in FIGS. 2A to 2D and accordingly those similar components and elements are denoted by like numerals.

The nasal dilator 700 comprises a platform 702 spanning the aperture 114 defined by the inner surface 106 of the loop structure 104. For example, the platform 702 may comprise a mesh. In some embodiments the platform 702 may be releaseably coupled or attached to the inner surface 106 of the nasal dilator 700, for example by a snap fit or interference fit.

In some embodiments, platform 702 may comprise a filter 704. The filter 704 may be composed of a fine woven mesh or an open celled porous material, such as a foam or compressed fibre. The filter 704 may be employed to filter out airborne particles such as bacteria, dust, pollens, and/or other allergens. In some embodiments, the filter 704 may be replaceable and may be arranged to be removeably connected, or "snap-fit" to the inner surface 106 of the loop structure 104. Alternatively, the filter 704 may be integrally formed with, or may be welded or ultrasonically welded to the loop structure 104.

Figure 8:
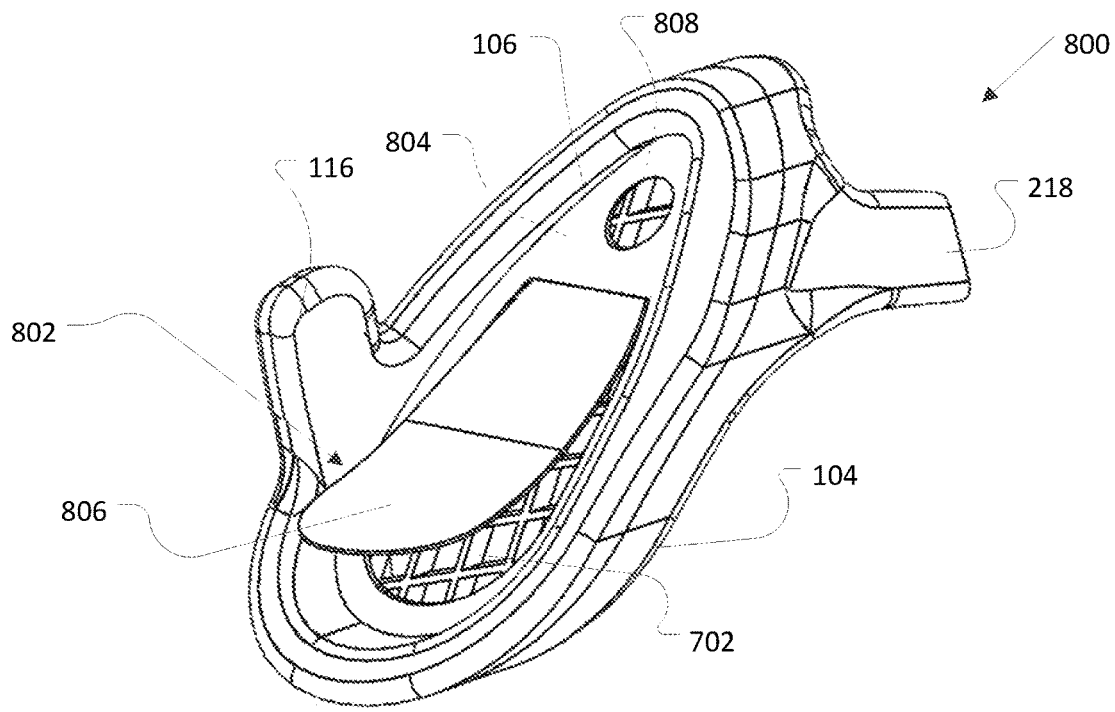
FIG. 8 is a rear perspective view of a nasal dilator including a valve system, according to some embodiments.

Referring now to FIG. 8, there is illustrated a nasal dilator, generally indicated at 800, according to some embodiments.

The nasal dilator 800 may comprise similar components and elements to those of nasal dilator device 200 as depicted in FIGS. 2A to 2D and dilator device 700 as depicted in FIG. 7 and accordingly those similar components and elements are denoted by like numerals.

The nasal dilator 800 comprises a valve mechanism 802 to allow for control of flow of fluid, such as air, through the aperture 114 defined by the inner surface 106 of the loop structure 104. In some embodiments, as depicted in FIG. 8, the valve mechanism 802 comprises a seal 804 supported by the platform 702 and which may span the aperture 114 of the loop structure 104. The seal 804 may form a seal with the inner surface 106 of the loop structure 104.

The seal comprises a flap 806 configured to transition between an open state, whereby fluid, such as air, may be conveyed through the platform 702 and a closed state, whereby fluid, such as air, may be hindered or substantially blocked from being conveyed through the platform 702 by the flap 806. In some embodiments, an orifice 808 may be disposed in the seal 804. In some embodiments, the seal 804, the flap 806 and the platform 702 may be configured to act as a one-way valve, for example, to allow fluid flow, for example, airflow, through the valve mechanism 802 substantially in a single direction only. In some embodiments, the valve mechanism 802 is configured to create a controllable and adjustable positive expiratory air pressure (PEAP) within the nasal cavity. The size of the orifice 808 may be selected to control or at least substantially influence PEAP within the nasal cavity of the nose 304.

Figure 9:
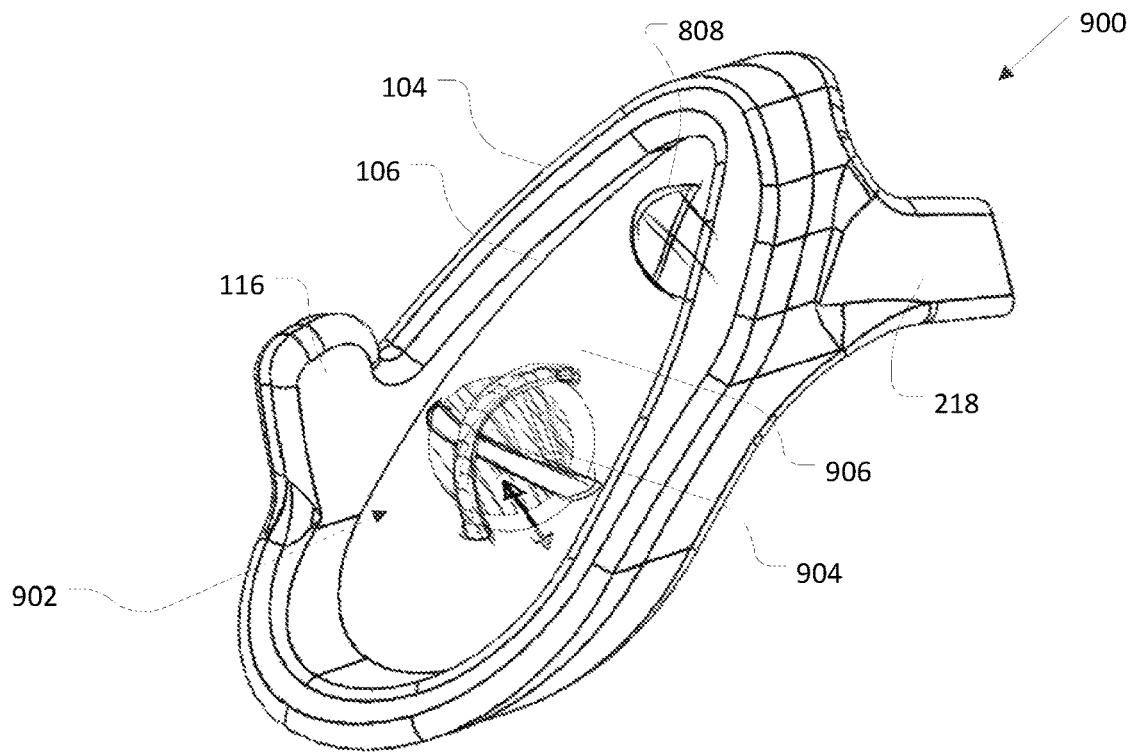
FIG. 9 is a rear perspective view of a nasal dilator including a valve system, according to some embodiments.

Referring now to FIG. 9, there is illustrated a nasal dilator, generally indicated at 900, according to some embodiments. The nasal dilator 900 may comprise similar components and elements to those of nasal dilator 200 as depicted in FIGS. 2A to 2D and dilator device 700 as depicted in FIG. 7 and accordingly those similar components and elements are denoted by like numerals.

The nasal dilator 900 comprises a valve mechanism 902 to allow for control of fluid flow, for example, airflow, through the aperture 114, as defined by the inner surface 106 of the loop structure 104. As depicted in FIG. 9, the valve mechanism 902 of nasal dilator 900 comprises a ball valve 904 and a seal 906 arranged upon the platform 702. The ball valve may be configured to transition between an open state, whereby fluid, such as air, may be conveyed through the platform, and a closed state, whereby fluid, such as air, may be hindered or substantially blocked from being conveyed through the platform by the ball valve. The seal 906 may be supported by the platform 702 and may span the aperture 114 of the loop structure 104. The seal 906 may form a seal with the inner surface 106 of the loop structure 104.

In some embodiments, an orifice 808 may be disposed in the seal 906. In some embodiments, the ball valve 904, the seal 906 and the platform 702 may be configured to perform as a one-way valve, for example, to allow fluid flow, for example, airflow, through the valve mechanism 902 substantially in a single direction only. In some embodiments, the valve mechanism 902 may create a controllable and adjustable PEAP within the nasal cavity of the nose 304.

By forming a seal with the nasal passage 306, the nasal dilators 700, 800 allow inhalation and exhalation through the nose 304 of the user to be at least somewhat controlled, as well as providing nasal dilation. Thus, the nasal dilators 700, 800 may be employed for treating snoring and obstructive sleep apnea (OSA). For example, OSA is caused by collapse of the nasal passage airway during sleep, which may result in periods of airflow restriction and/or cessation and may contribute to snoring. The nasal dilators 700, 800 make use of the user's own breathing to create positive nasal airway pressure to prevent or mitigate this obstructed breathing by reducing a capacity of the user to exhale through their nose and thereby increasing pressure within the nasal passages. In some embodiments, the nasal dilators 700, 800 allow a user to intake or inhale though the nose 304 while hindering a volume of air exhaled through the nose 304, thereby controlling or at least substantially influencing PEAP.

Figure 10A:
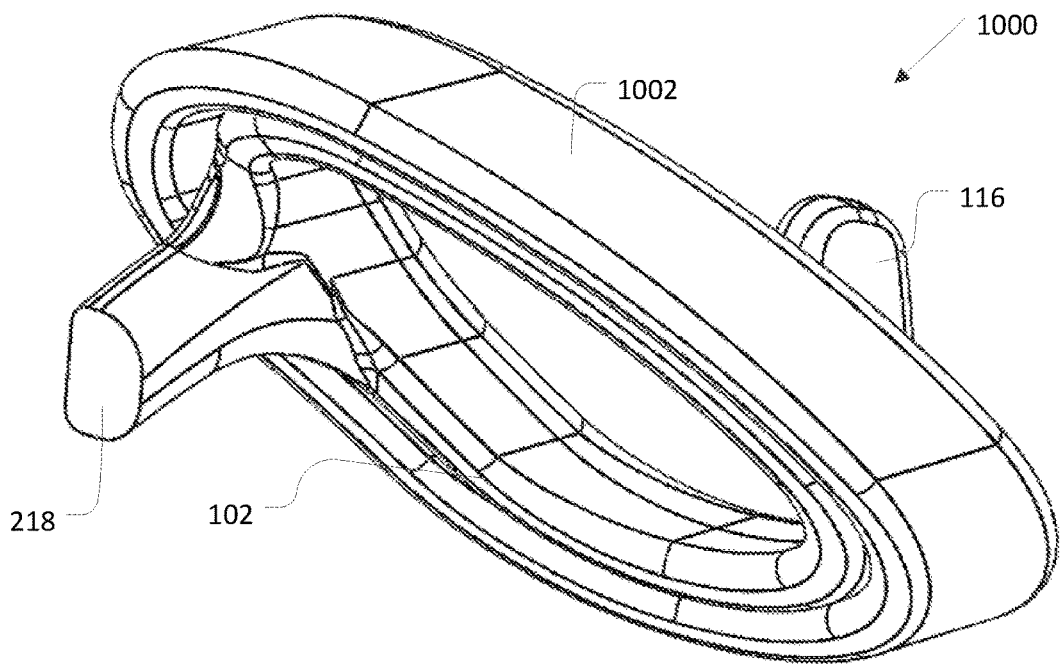
FIG. 10A is a front perspective view of a nasal dilator including an outer layer, according to some embodiments.
Figure 10B:
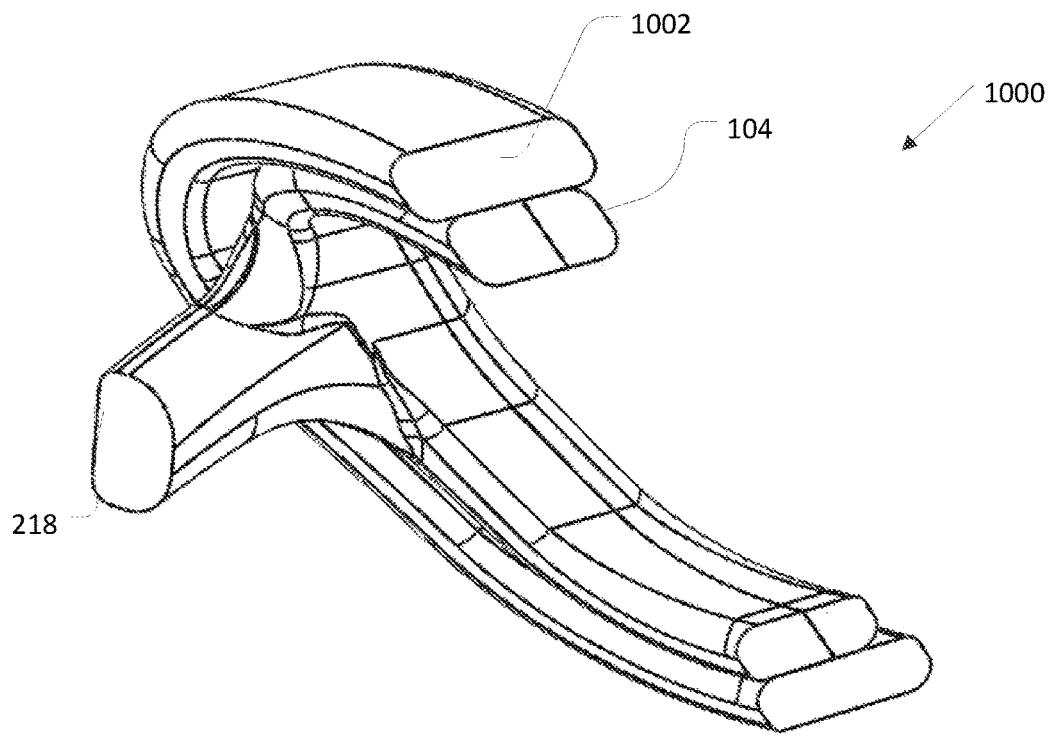
FIG. 10B is a cut-away front perspective view of the nasal dilator of FIG. 10A.

Referring now to FIGS. 10A and 10B, there is illustrated a nasal dilator, generally indicated at 1000, according to some embodiments. The nasal dilator 1000 may comprise similar components and elements to those of nasal dilator device 200 as depicted in FIGS. 2A to 2D and accordingly those similar components and elements are denoted by like numerals.

In some embodiments, as depicted in FIGS. 10A and 10B, the nasal dilator 1000 comprises an outer layer 1002 disposed along the outer surface 108 of the loop structure 104. For example, the outer layer 1002 may extend along at least a section of a length of (and optionally all the way around) the outer surface 108 of the loop structure 104. The outer layer 1002 may be arranged to follow a contour of the nasal cavity of the user and form a seal with the nasal passage wall 302 to substantially seal or block fluid flow, for example, airflow, between the outer surface 108 of the loop structure 104 of the body 102 and the nasal passage 306 of the nose 304 of the user.

In some embodiments, the outer layer 1002 may comprise a deformable material, such as a memory foam or an over mould. The over mould may be infused with a medicament and/or a fragrance. The outer layer 1002 may be formed of a soft elastomeric material, for example. A thickness of the outer layer 1002 may be selected to accommodate a distance between the outer surface 108 of the loop structure 104 and the nasal passage 306 of a user.

Figure 11:
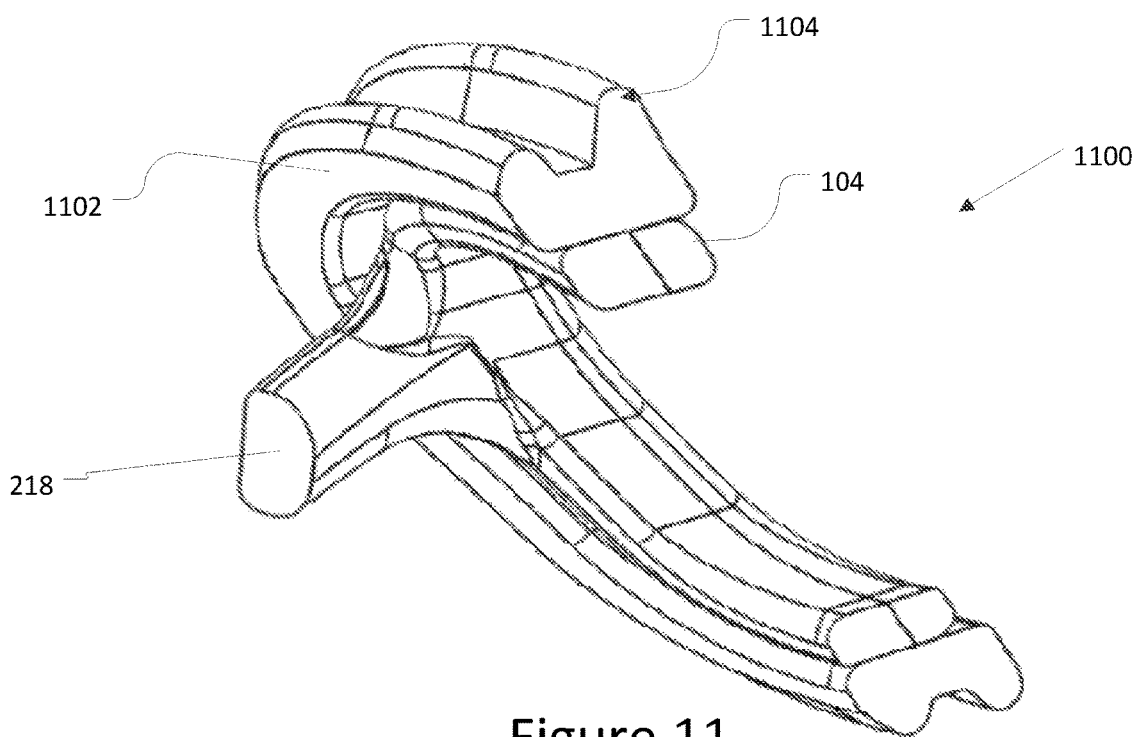
FIG. 11 is a cut-away front perspective view of a nasal dilator including an outer layer according to some embodiments.

Referring now to FIG. 11, there is illustrated a partial cut away view of a nasal dilator, generally indicated at 1100, according to some embodiments. The nasal dilator 1100 may comprise similar components and elements to those of nasal dilator device 200 as depicted in FIGS. 2A to 2D and accordingly those similar components and elements are denoted by like numerals.

As depicted in FIG. 11, the nasal dilator 1100 comprises an outer layer 1102 disposed along the outer surface 108 of the loop structure 104. The outer layer 1102 comprises a protruding double flange portion 1104 extending along at least a section of a length of (and optionally all the way around) the outer surface 108 of the loop structure 104. In some embodiments, the outer layer 1102 comprises a deformable material, such as a memory foam or an over mould. The over mould may be infused with a medicament and/or a fragrance. The outer layer 1102 may be formed of a soft elastomeric material, for example.

Figure 12:
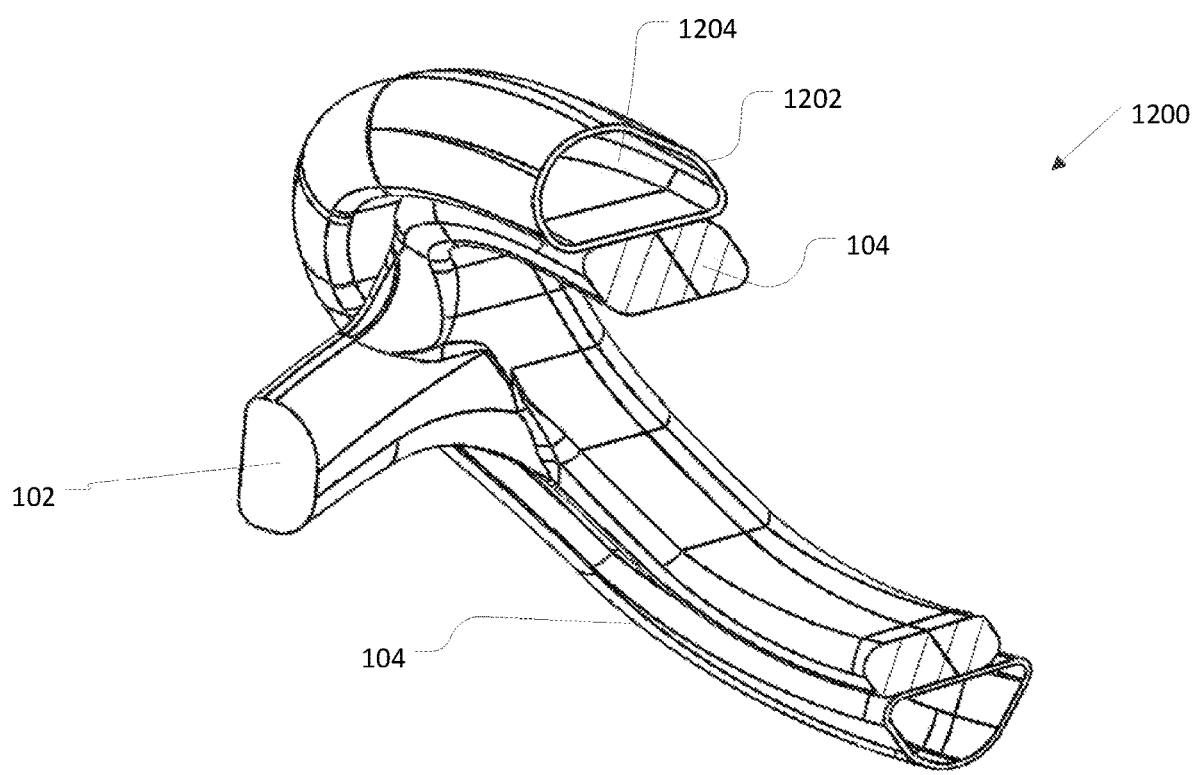
FIG. 12 is a cut-away front perspective view of a nasal dilator including an outer layer according to some embodiments.

Referring now to FIG. 12, there is illustrated a nasal dilator, generally indicated at 1200, according to some embodiments. The nasal dilator 1200 may comprise similar components and elements to those of nasal dilator device 200 as depicted in FIGS. 2A to 2D and accordingly those similar components and elements are denoted by like numerals.

As depicted in FIG. 12, the nasal dilator 1200 comprises an outer layer 1202 disposed along the outer surface 108 of the loop structure 104. The outer layer 1202 comprises a deformable tube 1204 extending along at least a section of a length of (and optionally all the way around) the outer surface 108 of the loop structure 104. The outer layer 1202 may be formed of a soft elastomeric material, for example. The outer layer 1202 may be arranged to follow a contour of the nasal passage 306 of the user and form a seal with the nasal passage wall 302 to substantially seal fluid flow, for example, airflow, between the outer surface 108 of the loop structure 104 of the body 102 and the nasal passage 306 of the user. In some embodiments, the tube 1204 may be inflatable.

Figure 13:
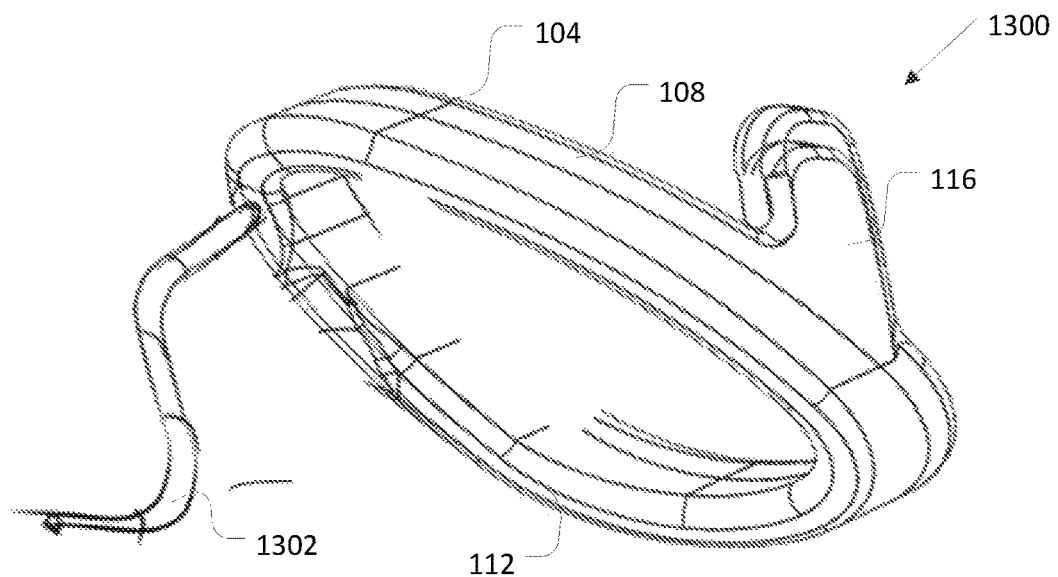
FIG. 13 is a front perspective view of a nasal dilator including a tether according to some embodiments.

Referring now to FIG. 13, there is illustrated a nasal dilator, generally indicated at 1300, according to some embodiments. The nasal dilator 1300 may comprise similar components and elements to those of nasal dilator device 100 as depicted in FIG. 1 and accordingly those similar components and elements are denoted by like numerals. In particular, the nasal dilator 1300 comprises a tether 1302 to allow for extraction and/or adjustment of the nasal dilator 1300 once it is inserted in a user's nose 304. The tether 1302 may comprise a thin plastic or wire filament and may be connected to the body 102 at a position on an outer or front side or edge of the loop structure 104, for example.

Figure 14:
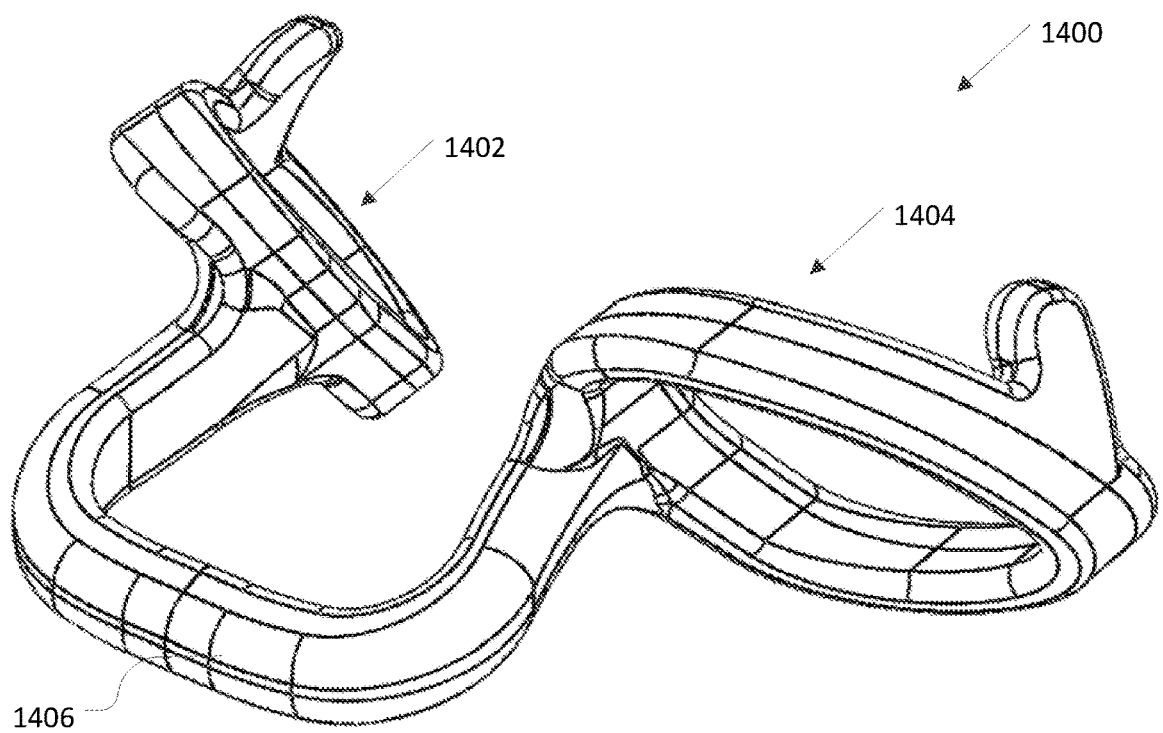
FIG. 14 is a front perspective view of a nasal dilator device comprising the nasal dilator of FIGS. 2A to 2D tethered or connected to another nasal dilator of FIGS. 2A to 2D, according to some embodiments.

Referring now to FIG. 14, there is illustrated a nasal dilator device, generally indicated at 1400, according to some embodiments. The nasal dilator device 1400 comprises a first nasal dilator 1402 and a second nasal dilator 1404. The nasal dilators 1402 and 1404 may comprise similar components and elements to those of nasal dilator device 200 as depicted in FIGS. 2A to 2D and accordingly those similar components and elements are denoted by like numerals. As depicted in FIG. 14, the nasal dilator device 1400 comprises a coupling, such as a substantially U-shaped clip or bridge 1406, to connect or couple the leg member 218 of the first nasal dilator 1402 to the leg member 218 of the second nasal dilator 1404. In other embodiments, the coupling comprises a tether (not shown) to connect the leg member 218 of the first nasal dilator 1402 to the leg member 218 of the second nasal dilator 1404.

Figure 15:
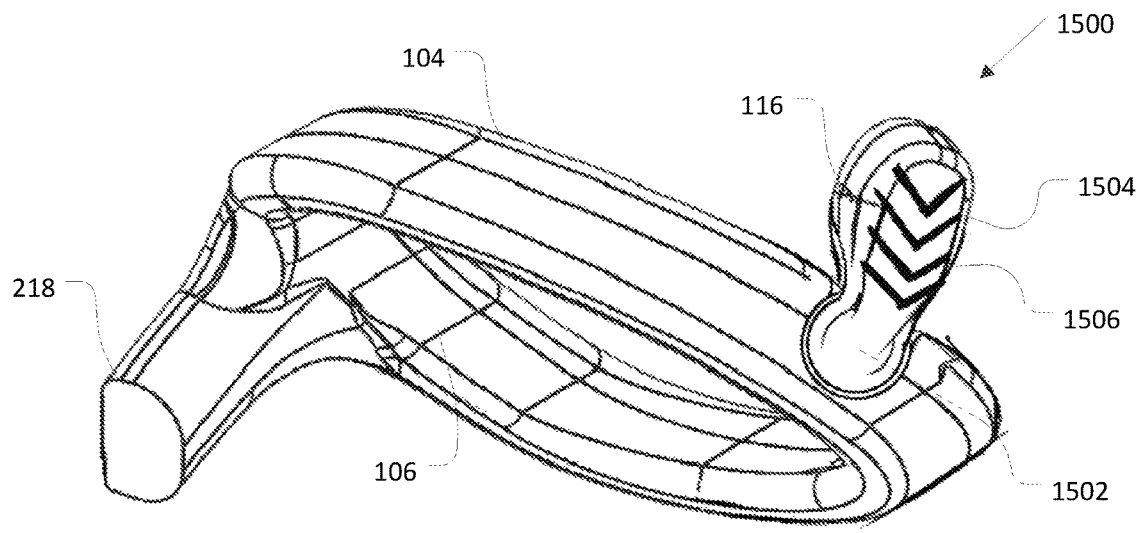
FIG. 15 is a front perspective view of a nasal dilator including an adjustable arm, according to some embodiments.

Referring now to FIG. 15, there is illustrated a nasal dilator, generally indicated at 1500, according to some embodiments. The nasal dilator 1500 may comprise similar components and elements to those of nasal dilator 200 as depicted in FIGS. 2A to 2D and accordingly those similar components and elements are denoted by like numerals.

In some embodiments, as depicted in FIG. 15, the arm member 116 of the nasal dilator 1500 is moveably coupled to the loop structure 104. For example, the arm member 116 may be rotatably coupled or hingedly coupled to the loop structure 104 to change its angle of projection relative to the plane of the loop structure 104. In some embodiments, the arm member 116 may comprise a ball and socket joint 1502 to couple the arm member 116 to the loop structure 104. The ball and socket joint 1502 may allow for selective positioning of the arm member 116. The coupling of the ball and socket joint 1502 may be substantially stiff to enable the arm member 116 stay in position once positioned by the user.

In some embodiments, the arm member 116 of the nasal dilator 1500 comprises a nostril engaging element 1504 having an outwardly facing engagement surface to engage with the nasal passage wall 302 of the nose 304. The nostril engaging element 1504 may comprise a relatively large proportion of the surface area of the arm member 116.

In some embodiments, the nostril engaging element 1504 is provided with a series of protrusions 1506 on the outwardly facing engagement surface. The protrusions 1506 may be composed of a relatively soft over mould material, for example a polymer material such as thermoplastic elastomer (TPE) and/or may be provided as fins or fin-like structures to provide a comfortable and/or grippable surface for engaging with the nasal passage walls 302 of the nose 304. The nostril engaging element 1504 may be substantially oval, rectangular, triangular or truncated triangular in shape. In some embodiments, the protrusions 1506 may form a u-shaped pattern, a v-shaped pattern, or elongated v or ✓ (tick) shaped pattern, such as a chevron design, comprising a plurality of aligned u-shaped, v-shaped or elongated v or ✓ (tick) shaped protrusions 1506.

In some embodiments, the position of the arm member 116 may be adjusted by the user prior to insertion. In some embodiments, the arm member 116 may be configured to self-adjust during insertion and positioning by the user.

Figure 16:
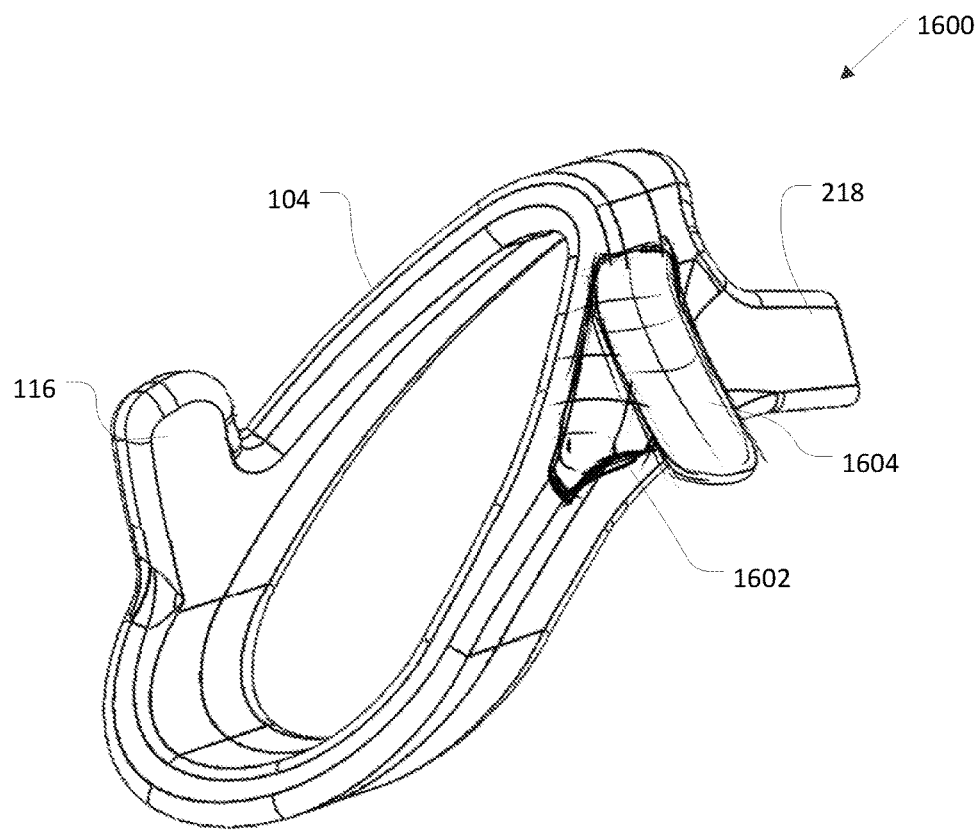
FIG. 16 is a rear perspective view of a nasal dilator including a chamber, according to some embodiments.

Referring now to FIG. 16, there is illustrated a nasal dilator, generally indicated at 1600, according to some embodiments. The nasal dilator 1600 may comprise similar components and elements to those of nasal dilator 200 as depicted in FIGS. 2A to 2D and accordingly those similar components and elements are denoted by like numerals.

The loop structure 104 of nasal dilator 1600 comprises a chamber 1602 arranged to receive a compound, such as a fragrance/aromatic agent or a medicament. The chamber may be positioned in a portion of the loop structure 104 adjacent where the leg member 218 extends from the body 102 or at another suitable location, such as on the arm member 116, for example. The chamber 1602 may be positioned to open outwardly from the outer surface 108 or inwardly from the inner surface 106. The chamber 1602 may be covered or coverable by a removable seal 1604. For example, the seal 1604 may be removed by the user just prior to insertion of the device into the nostril of the user. In this way, the medicament and/or fragrance or aromatic agent is released only when the seal 1604 is removed, thereby increasing a longevity or "shelf-life" and/or protecting the integrity of the medicament and/or aromatic agent. The agent may be an aromatic scent, such as an essential oil blend or synthetic fragrance blend to provide an olfactory and/or physiological response such as decongesting the nasal passage 306, promoting relaxation, promoting sleepiness, suppressing appetite, or a medicament, such as a drug to reduce pain such as a migraine.

Figure 17A:
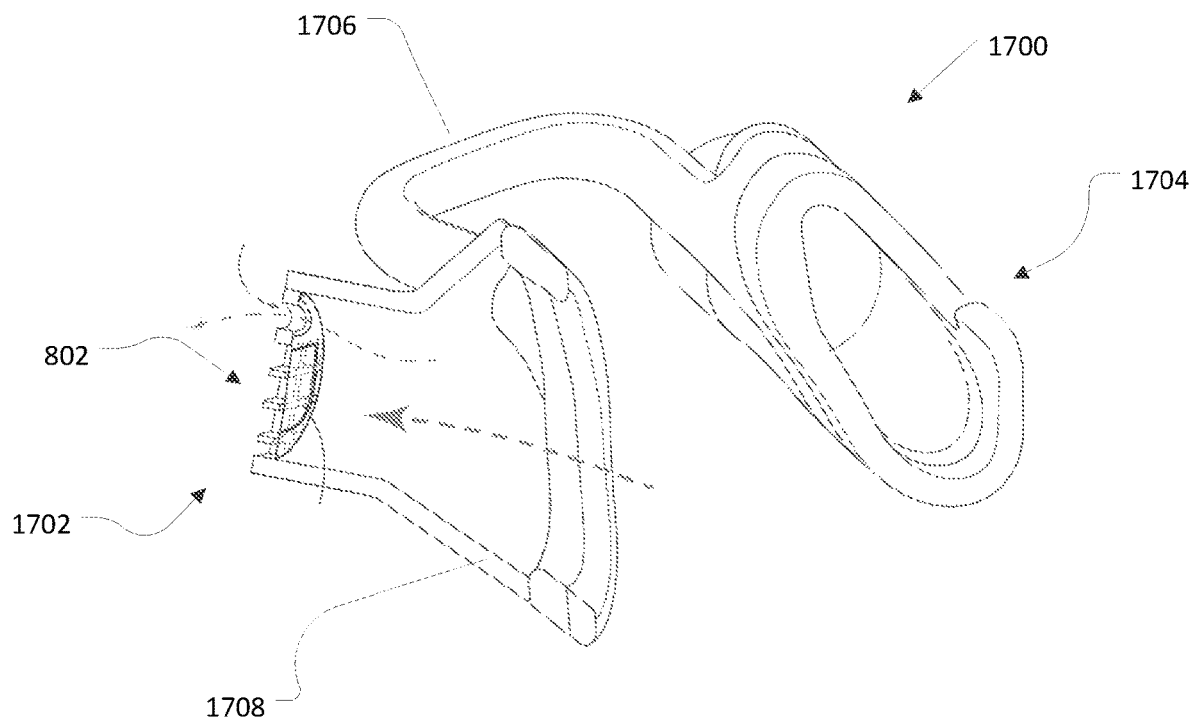
FIG. 17A is a front perspective view of a nasal dilator device including first and second nasal dilators having a collar and a valve mechanism, wherein the valve mechanism is in the closed state.
Figure 17B:
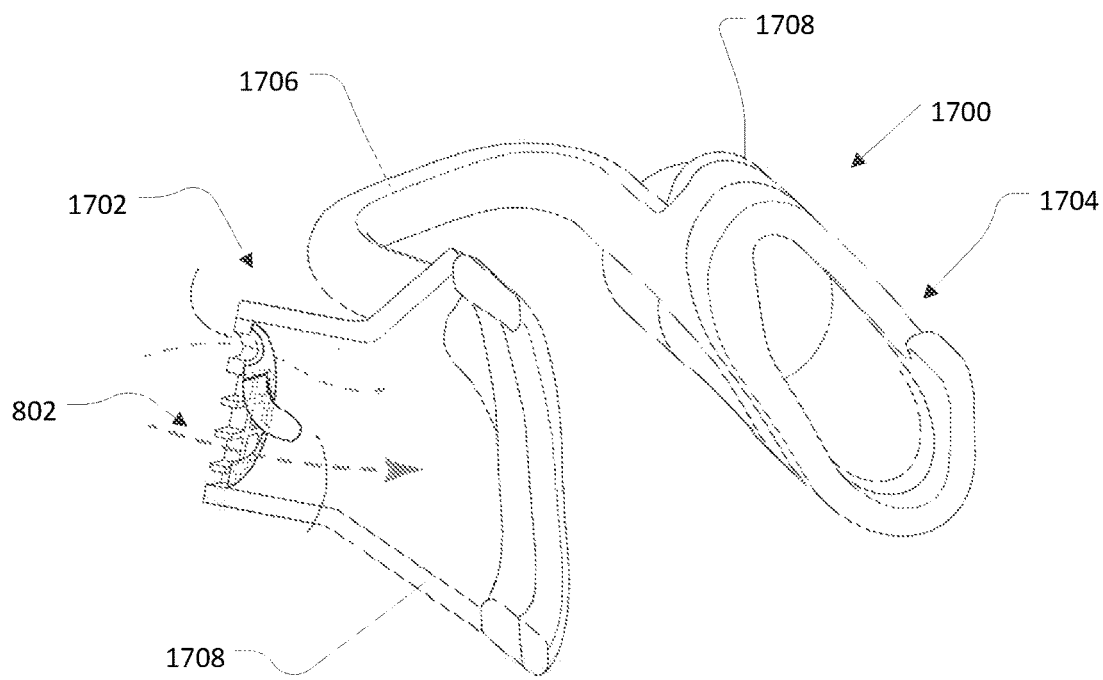
FIG. 17B is a front perspective view of the nasal dilator device of FIG. 17A wherein the valve mechanism is in the open state.

Referring now to FIGS. 17A and 17B, there is illustrated a nasal dilator device, generally indicated at 1700, according to some embodiments. The nasal dilator device 1700 comprises a first nasal dilator 1702 coupled to a second nasal dilator 1704. For example, the first nasal dilator 1702 may be coupled to a second nasal dilator 1704 by a U-shaped bridge or clip 1706, as depicted in FIGS. 17A and 17B. The first and second nasal dilators 1702, 1704 may comprise similar components and elements to those of nasal dilator 800 as depicted in FIG. 8 and accordingly those similar components and elements are denoted by like numerals.

As depicted in FIGS. 17A and 17B, each of the first and second nasal dilators 1702, 1704 comprise a platform 702 and valve mechanism 802 as shown and described in relation to FIG. 8. The nasal dilator 1700 comprises a collar or shroud 1708 extending from the second side 112 of the loop structure 104 and forming a seal with the loop structure 104, for example, the inner surface 106 of the loop structure 104. The collar or shroud 1708 acts as an extension to separate the valve mechanism 802 of the nasal dilator 1700 from the dilation function of the loop structure 104. The collar or shroud may have a narrowing or tapering section to transition between the second side 112 of the loop structure 104, which may have a larger aperture, and the valve mechanism 802, which may have a smaller size and define a smaller air flow aperture than the loop structure 104. In some embodiments, the collar or shroud 1708 may be integrally formed with, or connected to, the valve mechanism 802 and the collar or shroud 1708 may be removably coupled to the second side 112.

FIG. 17A shows the valve mechanism 802 of the nasal dilator 1700 in a substantially closed state, in which air is free to flow only through the aperture 808 (as it air flow is blocked or obscured by the closed flap 806), and FIG. 17B shows the valve mechanism 802 of the nasal dilator 1700 in a substantially open state, in which air is free to flow through the filter 704 (as it is not blocked or obscured by the open flap 806) and through the aperture 808. The flap 806 can readily deflect from a position in which it covers an aperture over the filter 704 and blocks air flow therethrough, to a position in which it swings open while remaining attached to the platform 702 and thus allows air to pass through the aperture over the filter. The flap 806 (and thus the valve 802) transitions between the open and closed states depending on whether the user is inhaling (open) or exhaling (closed).

Figure 18A:
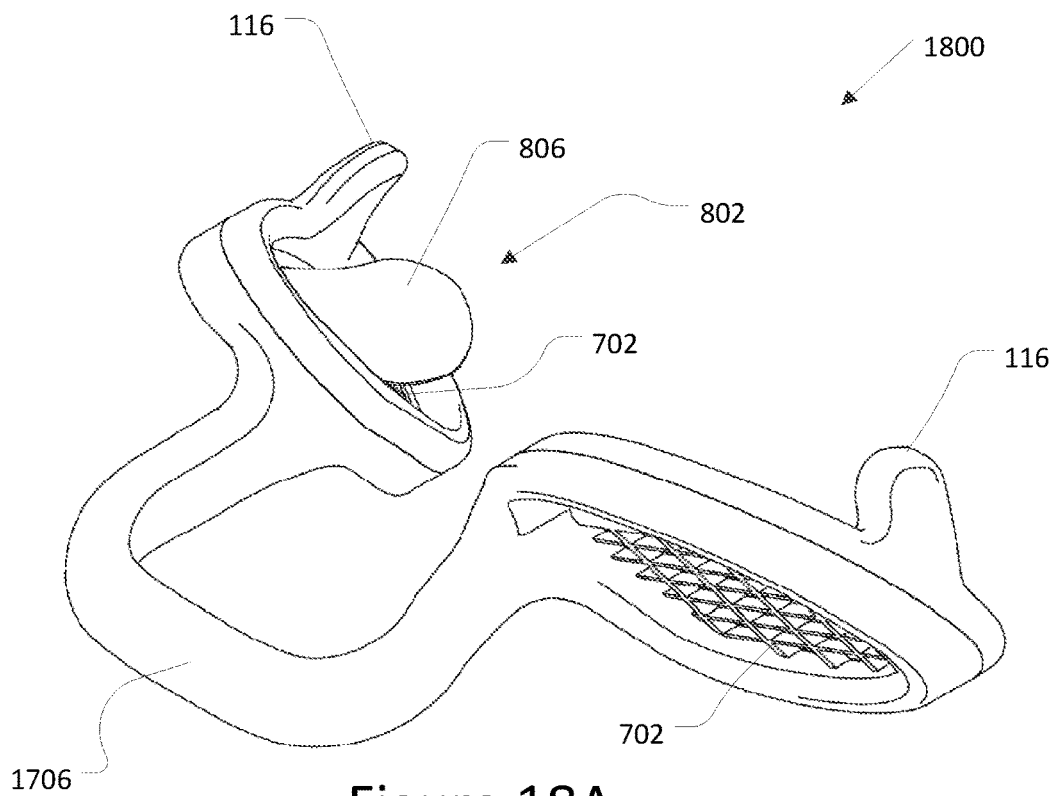
FIG. 18A is a front perspective view of a nasal dilator device including first and second nasal dilators having a valve.
Figure 18B:
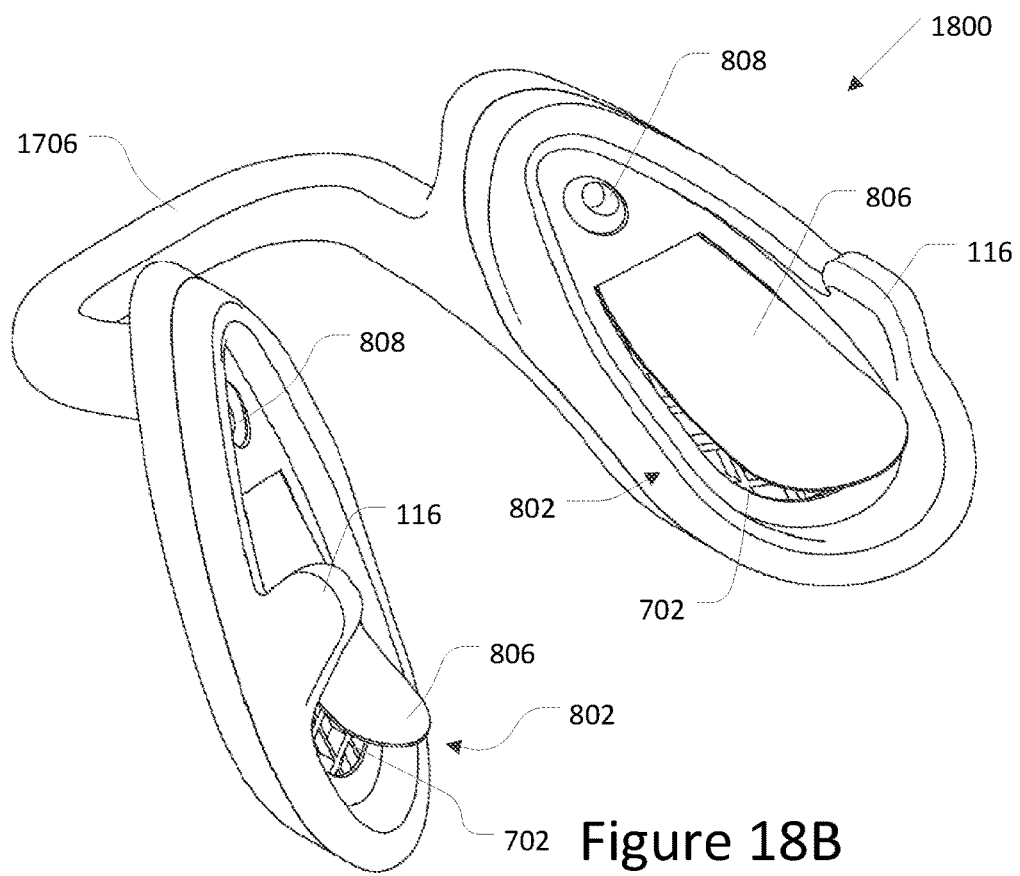
FIG. 18B is a rear perspective view of a nasal dilator device including first and second nasal dilators having a valve.

FIGS. 18A and 18B illustrate a nasal dilator device, generally indicated at 1800, according to some embodiments. The nasal dilator device 1800 comprises two dilators joined by a clip or bridge 1706. The first and second nasal dilators may comprise similar components and elements to those of nasal dilator 800 as depicted in FIG. 8 and accordingly those similar components and elements are denoted by like numerals. Each of the nasal dilators has a platform 702, optionally with a filter 704, which is substantially covered by a flap 806 that acts as a one-way valve. The cover portion 804 that comprises the flap 806 also defines an aperture 808 to allow passage of a small amount of air. The flaps 806 of the two dilators 800 in device 1800 operate in the same way as is described above in relation to FIGS. 17A and 17B. Device 1800 is similar to device 1700 except that no shroud or collar is employed to separate the dilation function provided by the loop structure 104 from the valve mechanism 802.

In some embodiments, the nasal dilator 100, 200, 400, 500, 600, 700, 800, 900, 1000, 1100, 1200, 1300, 1600, 1700 or 1800 may comprise at least one coating or film (not shown) from which a fragrance, aroma or medicament may be released. For example, in some embodiments, the film may be arranged to release a fragrance, aroma or medicament in response to abrasion, such as scratching or scraping. The film may be provided with an outer cover, seal or strip to protect the film from unintended abrasion.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A nasal dilator comprising a body for insertion into a nasal cavity of a nose, the body including:
    a loop structure having an inner surface, a reverse outer surface, a first side and a second side opposite to the first side, wherein the inner surface defines an aperture and the reverse outer surface is configured for urging against a nasal passage wall of the nose;
    an arm member having a first end coupled to the loop structure and a free end, the arm member extending outwardly from the loop structure in a plane substantially parallel to the outer surface of the loop structure so as to extend along a nasal passage of the nasal cavity and engage with an internal surface of a nostril of the nose;

a leg member extending outwardly from the loop structure and configured to protrude from the nasal cavity of a user, wherein the arm member extends from the first side of the loop structure and the leg member extends from the second side of the loop structure;

a platform spanning the aperture defined by the inner surface of the loop structure; and a valve for controlling fluid flow through the aperture.

2. The nasal dilator of claim 1, wherein the platform is releasably coupled to the inner surface of the loop structure.

3. The nasal dilator of claim 1, wherein the platform comprises a filter.

4. The nasal dilator of claim 1, wherein the valve comprises a seal supported by the platform and configured to span the aperture defined by the inner surface of the loop structure.

5. The nasal dilator of claim 4, wherein the seal includes a flap configured to transition between an open state, whereby fluid may be conveyed through the platform, and a closed state, whereby fluid may be hindered from being conveyed through the platform by the flap and wherein an orifice is disposed in the seal.

6. The nasal dilator of claim 4, wherein the seal includes a ball valve configured to transition between an open state, whereby fluid may be conveyed through the platform, and a closed state, whereby fluid may be hindered from being conveyed through the platform by the ball valve and wherein an orifice is disposed in the seal.

7. The nasal dilator of claim 1, wherein the valve comprises a collar extending from the second side of the loop structure and forming a seal with the loop structure.

8. The nasal dilator of claim 1, wherein the arm member comprises a nostril engaging element at the free end to engage with the internal surface of the nostril.

9. The nasal dilator of claim 8, wherein the nostril engaging element comprises a series of protrusions disposed on the nostril engaging element.

10. A nasal dilator comprising a body for insertion into a nasal cavity of a nose, the body including:

a loop structure having an inner surface and a reverse outer surface, wherein the inner surface defines an aperture;

an arm member, the arm member extending outwardly from the loop structure in a plane substantially parallel to the outer surface of the loop structure;

a leg member extending outwardly from the loop structure and configured to protrude from the nasal cavity of a user, wherein the arm member extends from a first side of the loop structure and the leg member extends from a second side of the loop structure;

a platform spanning the aperture defined by the inner surface of the loop structure; and a valve for controlling fluid flow through the aperture;

wherein the outer surface of the loop structure is arranged, in use, to urge against a nasal cavity wall in proximity to a nasal vestibule of the nose to allow dilation of a nostril of the nose and the arm member is arranged, in use, to extend along the nasal passage and to engage with an internal surface of the nostril.

11. The nasal dilator of claim 10, wherein the arm member extends beyond a perimeter of the loop structure and is configured, in use, to exert an outward force on the internal surface of the nostril to thereby stent and/or dilate the nostril.

* * * * *